(12) United States Patent
Gorfinkel et al.

(10) Patent No.: US 12,329,358 B2
(45) Date of Patent: Jun. 17, 2025

(54) INTRAORAL SCANNER SLEEVE

(71) Applicant: Align Technology, Inc., San Jose, CA (US)

(72) Inventors: Roee Gorfinkel, Yavne (IL); Eran Ishay, Tel Aviv (IL); Benny Gordon, Hod HaSharon (IL); Avi Kopelman, Palo Alto, CA (US); Nir Makmel, Tel Aviv (IL)

(73) Assignee: Align Technology, Inc., San Jose, CA (US)

( * ) Notice: Subject to any disclaimer, the term of this patent is extended or adjusted under 35 U.S.C. 154(b) by 367 days.

(21) Appl. No.: 17/747,894

(22) Filed: May 18, 2022

(65) Prior Publication Data

US 2022/0369910 A1 Nov. 24, 2022

Related U.S. Application Data

(60) Provisional application No. 63/189,915, filed on May 18, 2021.

(51) Int. Cl.
*A61B 1/00* (2006.01)
*A61B 1/24* (2006.01)

(52) U.S. Cl.
CPC ............ *A61B 1/00142* (2013.01); *A61B 1/24* (2013.01)

(58) Field of Classification Search
None
See application file for complete search history.

(56) References Cited

U.S. PATENT DOCUMENTS

| | | | | |
|---|---|---|---|---|
| 3,769,980 A | * | 11/1973 | Karman | A61B 1/32 600/220 |
| 4,279,247 A | * | 7/1981 | Kinoshita | A61B 1/00181 600/173 |
| 5,408,992 A | * | 4/1995 | Hamlin | A61B 5/0088 600/109 |
| 5,484,283 A | * | 1/1996 | Franetzki | A61B 1/042 433/116 |
| 5,695,448 A | * | 12/1997 | Kimura | A61B 1/0005 600/125 |
| 6,095,811 A | * | 8/2000 | Stearns | A61B 1/00142 600/125 |
| 6,099,314 A | | 8/2000 | Kopelman et al. | |
| 6,334,772 B1 | | 1/2002 | Taub et al. | |
| 6,334,853 B1 | | 1/2002 | Kopelman et al. | |

(Continued)

FOREIGN PATENT DOCUMENTS

GB 80904540001000 2/2016
JP 1577736 S 5/2017

(Continued)

OTHER PUBLICATIONS

ITero Scanner; Introducing the iTero Element Plus Series; (Screenshot); 1 page; retrieved from the internet at YouTube (https://www/youtube.com/watch?v=VSQMPgW1vSs) on Jul. 12, 2024; available as of Mar. 3, 2021.

(Continued)

*Primary Examiner* — John P Leubecker
*Assistant Examiner* — Jae Woo
(74) *Attorney, Agent, or Firm* — Shay Glenn LLP

(57) ABSTRACT

Apparatuses, including sleeves, intraoral scanning systems to use these sleeves, and methods of using the sleeve.

34 Claims, 24 Drawing Sheets

(56) References Cited

U.S. PATENT DOCUMENTS

| | | | |
|---|---|---|---|
| 6,379,296 B1 * | 4/2002 | Baggett | A61B 1/303 |
| | | | 600/179 |
| 6,463,344 B1 | 10/2002 | Pavlovskaia et al. | |
| 6,542,249 B1 | 4/2003 | Kofman et al. | |
| 6,633,789 B1 | 10/2003 | Nikolskiy et al. | |
| 6,664,986 B1 | 12/2003 | Kopelman et al. | |
| 6,697,164 B1 | 2/2004 | Babayoff et al. | |
| 6,845,175 B2 | 1/2005 | Kopelman et al. | |
| 6,867,864 B2 * | 3/2005 | Overbeck | A61B 1/00052 |
| | | | 356/402 |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,914,442 B1 * | 3/2011 | Gazdzinski | A61B 1/00156 |
| | | | 600/128 |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| D818,579 S | 5/2018 | Yao | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,258,227 B1 * | 4/2019 | Wilson | A61B 1/0014 |
| 10,380,212 B2 | 8/2019 | Elbaz et al. | |
| 10,390,913 B2 | 8/2019 | Sabina et al. | |
| D862,692 S | 10/2019 | Leon Rovira et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| D875,925 S | 2/2020 | Archat et al. | |
| D884,175 S | 5/2020 | Aubailly et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,813,727 B2 | 10/2020 | Sabina et al. | |
| 10,888,399 B2 | 1/2021 | Kopelman et al. | |
| D910,850 S | 2/2021 | Hansen et al. | |
| 10,952,816 B2 | 3/2021 | Kopelman | |
| D916,288 S | 4/2021 | Hansen et al. | |
| 10,980,613 B2 | 4/2021 | Shanjani et al. | |
| 10,986,982 B2 * | 4/2021 | Wu | A61B 1/00142 |
| 11,013,581 B2 | 5/2021 | Sabina et al. | |
| D925,739 S | 7/2021 | Shalev et al. | |
| 11,096,765 B2 | 8/2021 | Atiya et al. | |
| D941,464 S | 1/2022 | Nock et al. | |
| 11,238,586 B2 | 2/2022 | Minchenkov et al. | |
| 11,367,192 B2 | 6/2022 | Kopelman et al. | |
| D966,503 S | 10/2022 | Leard et al. | |
| D987,078 S | 5/2023 | Frenkler et al. | |
| D988,513 S | 6/2023 | Bassir | |
| D989,311 S | 6/2023 | Frenkler et al. | |
| 11,759,277 B2 * | 9/2023 | Shalev | A61B 46/17 |
| | | | 600/121 |
| 2002/0123664 A1 * | 9/2002 | Mitsumori | A61B 1/00188 |
| | | | 600/129 |
| 2003/0107652 A1 * | 6/2003 | Williams | A61B 1/042 |
| | | | 348/E5.025 |
| 2006/0048319 A1 * | 3/2006 | Morgan | A47L 13/17 |
| | | | 15/104.94 |
| 2006/0089627 A1 * | 4/2006 | Burnett | A61F 2/97 |
| | | | 606/1 |
| 2007/0007360 A1 * | 1/2007 | Ogino | A61B 1/051 |
| | | | 235/495 |
| 2007/0121786 A1 * | 5/2007 | Okawa | A61B 1/0615 |
| | | | 378/65 |
| 2008/0021276 A1 * | 1/2008 | Wax | A61B 1/00142 |
| | | | 600/122 |
| 2009/0069763 A1 * | 3/2009 | DiCarlo | A61M 1/684 |
| | | | 604/328 |
| 2010/0010308 A1 * | 1/2010 | Braun | A61B 1/00142 |
| | | | 600/121 |
| 2010/0041952 A1 * | 2/2010 | Castellucci | A61B 1/00165 |
| | | | 600/121 |
| 2010/0063359 A1 * | 3/2010 | Okoniewski | A61B 1/00142 |
| | | | 600/121 |
| 2010/0081878 A1 * | 4/2010 | Byers | A61B 1/00137 |
| | | | 600/125 |
| 2010/0273355 A1 * | 10/2010 | Gleason | A61B 1/00124 |
| | | | 439/638 |
| 2010/0308038 A1 * | 12/2010 | Davidson | B65D 81/264 |
| | | | 156/221 |
| 2011/0065991 A1 * | 3/2011 | Sarvazyan | A61B 1/31 |
| | | | 600/131 |
| 2011/0106029 A1 * | 5/2011 | Garren | A61B 10/0045 |
| | | | 604/319 |
| 2012/0029280 A1 * | 2/2012 | Kucklick | A61B 1/00183 |
| | | | 600/109 |
| 2012/0029289 A1 * | 2/2012 | Kucklick | A61B 1/00089 |
| | | | 600/156 |
| 2012/0077142 A1 * | 3/2012 | Maurer | A61K 6/78 |
| | | | 106/35 |
| 2012/0156634 A1 * | 6/2012 | Duff, Jr. | A61B 1/0016 |
| | | | 433/29 |
| 2012/0323069 A1 * | 12/2012 | Stout | A61B 1/307 |
| | | | 600/104 |
| 2013/0023770 A1 * | 1/2013 | Courtney | A61B 17/320758 |
| | | | 600/478 |
| 2016/0089002 A1 * | 3/2016 | Burton | A61B 1/00119 |
| | | | 600/154 |
| 2017/0027421 A1 * | 2/2017 | Imai | A61B 1/00137 |
| 2017/0112589 A1 * | 4/2017 | Ramkhelawan | A61B 1/00144 |
| 2017/0311781 A1 * | 11/2017 | O'Brien | A61M 5/1452 |
| 2018/0353062 A1 * | 12/2018 | Makmel | A61B 1/00142 |
| 2019/0029784 A1 | 1/2019 | Moalem et al. | |
| 2019/0150722 A1 * | 5/2019 | Yamaya | G02B 23/2476 |
| 2019/0258690 A1 * | 8/2019 | Elbaz | A61B 5/0088 |
| 2019/0269485 A1 * | 9/2019 | Elbaz | A61B 1/00016 |
| 2019/0275307 A1 * | 9/2019 | Kamler | A61B 1/00085 |
| 2019/0388193 A1 | 12/2019 | Saphier et al. | |
| 2020/0163533 A1 | 5/2020 | Kim et al. | |
| 2020/0187754 A1 * | 6/2020 | Furukawa | C08G 59/5033 |
| 2020/0281702 A1 | 9/2020 | Kopelman et al. | |
| 2020/0288959 A1 * | 9/2020 | Lahti | A61B 1/247 |

(56) References Cited

U.S. PATENT DOCUMENTS

| | | | |
|---|---|---|---|
| 2020/0315434 A1* | 10/2020 | Kopelman | A61B 1/00103 |
| 2020/0349705 A1 | 11/2020 | Minchenkov et al. | |
| 2020/0404243 A1 | 12/2020 | Saphier et al. | |
| 2021/0030503 A1* | 2/2021 | Shalev | A61C 9/0053 |
| 2021/0059796 A1 | 3/2021 | Weiss et al. | |
| 2021/0068773 A1 | 3/2021 | Moshe et al. | |
| 2021/0121049 A1* | 4/2021 | Rudnitsky | A61C 9/0053 |
| 2021/0128281 A1 | 5/2021 | Peleg | |
| 2021/0137653 A1 | 5/2021 | Saphier et al. | |
| 2021/0196152 A1 | 7/2021 | Saphier et al. | |
| 2021/0236110 A1* | 8/2021 | Williams | A61B 1/32 |
| 2021/0259535 A1* | 8/2021 | Shani | A61B 1/00096 |
| 2021/0369087 A1* | 12/2021 | Kodama | A61B 1/00096 |
| 2021/0401267 A1* | 12/2021 | Kodama | A61B 1/0676 |
| 2022/0079426 A1* | 3/2022 | Christiansen | A61B 1/00142 |
| 2022/0240770 A1* | 8/2022 | Sagiv | G02B 23/2476 |
| 2022/0409347 A1* | 12/2022 | Lee | G06F 3/016 |
| 2023/0218149 A1* | 7/2023 | Hansen | A61B 1/253 |
| | | | 361/600 |
| 2024/0164624 A1* | 5/2024 | Shalev | A61C 9/0053 |

FOREIGN PATENT DOCUMENTS

| | | |
|---|---|---|
| JP | 1601874 S | 4/2018 |
| JP | 1723255 S | 8/2022 |
| WO | D201984002 | 3/2019 |

OTHER PUBLICATIONS

Angelino et al.; Near-infrared imaging for detecting caries and structural deformities in teeth; IEEE journal of translational engineering in health and medicine; vol. 5; pp. 1-7; Apr. 19, 2017.

* cited by examiner

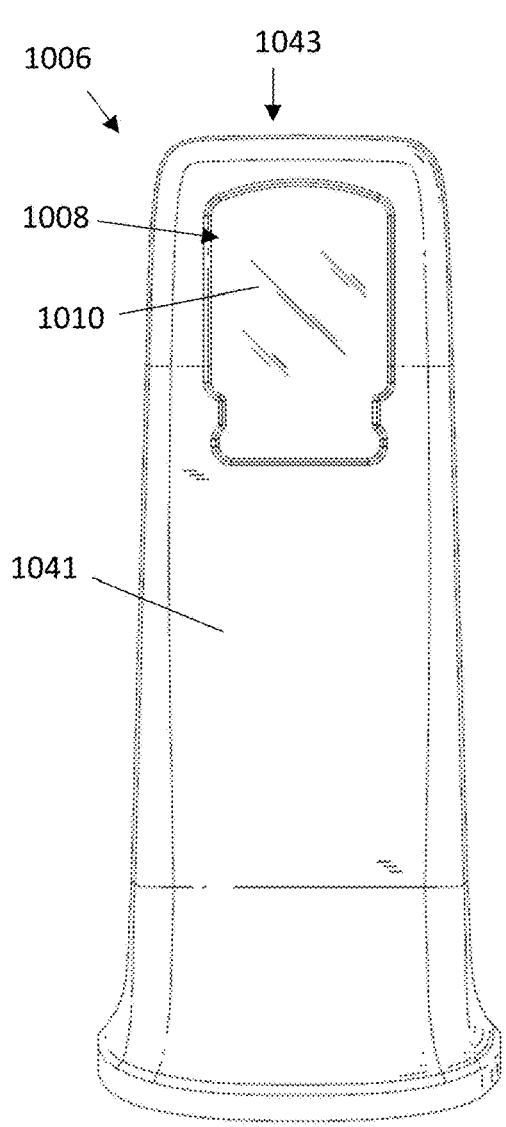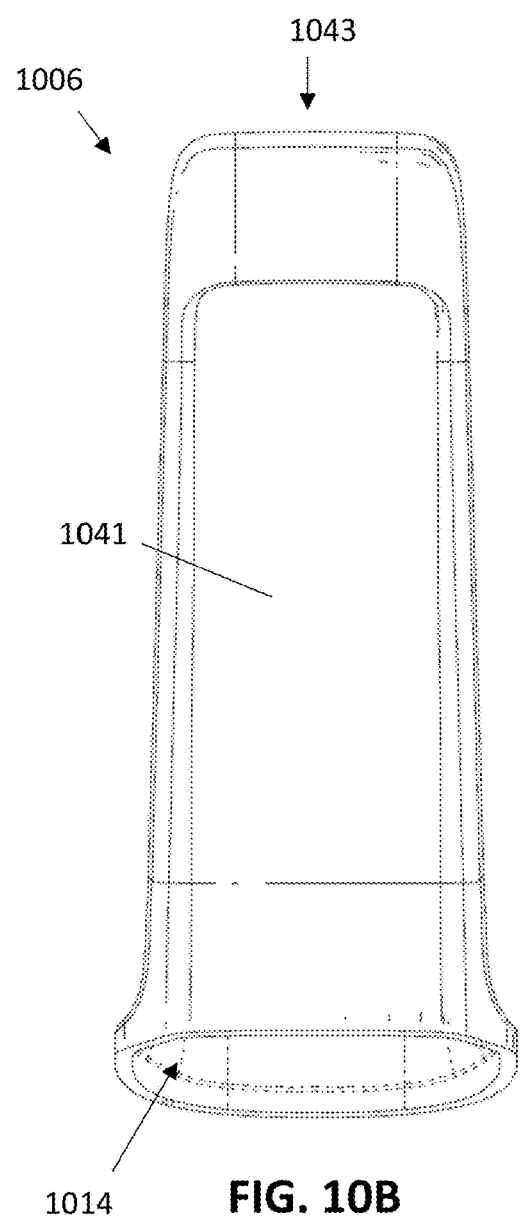
FIG. 10A  FIG. 10B
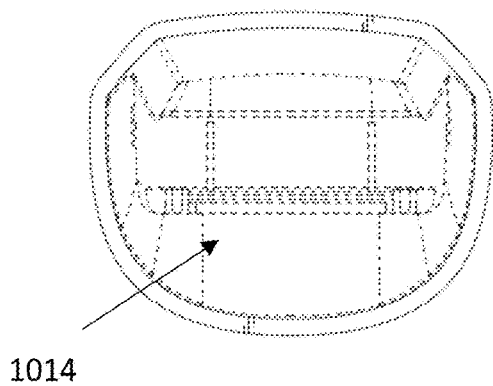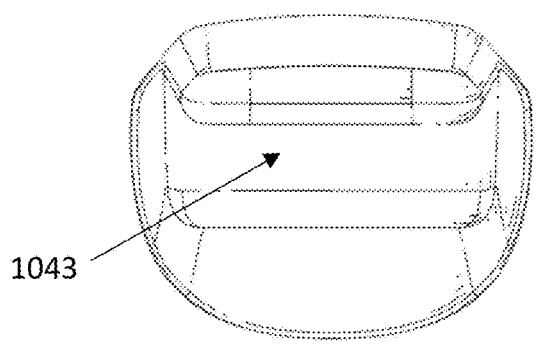
FIG. 10C  FIG. 10D

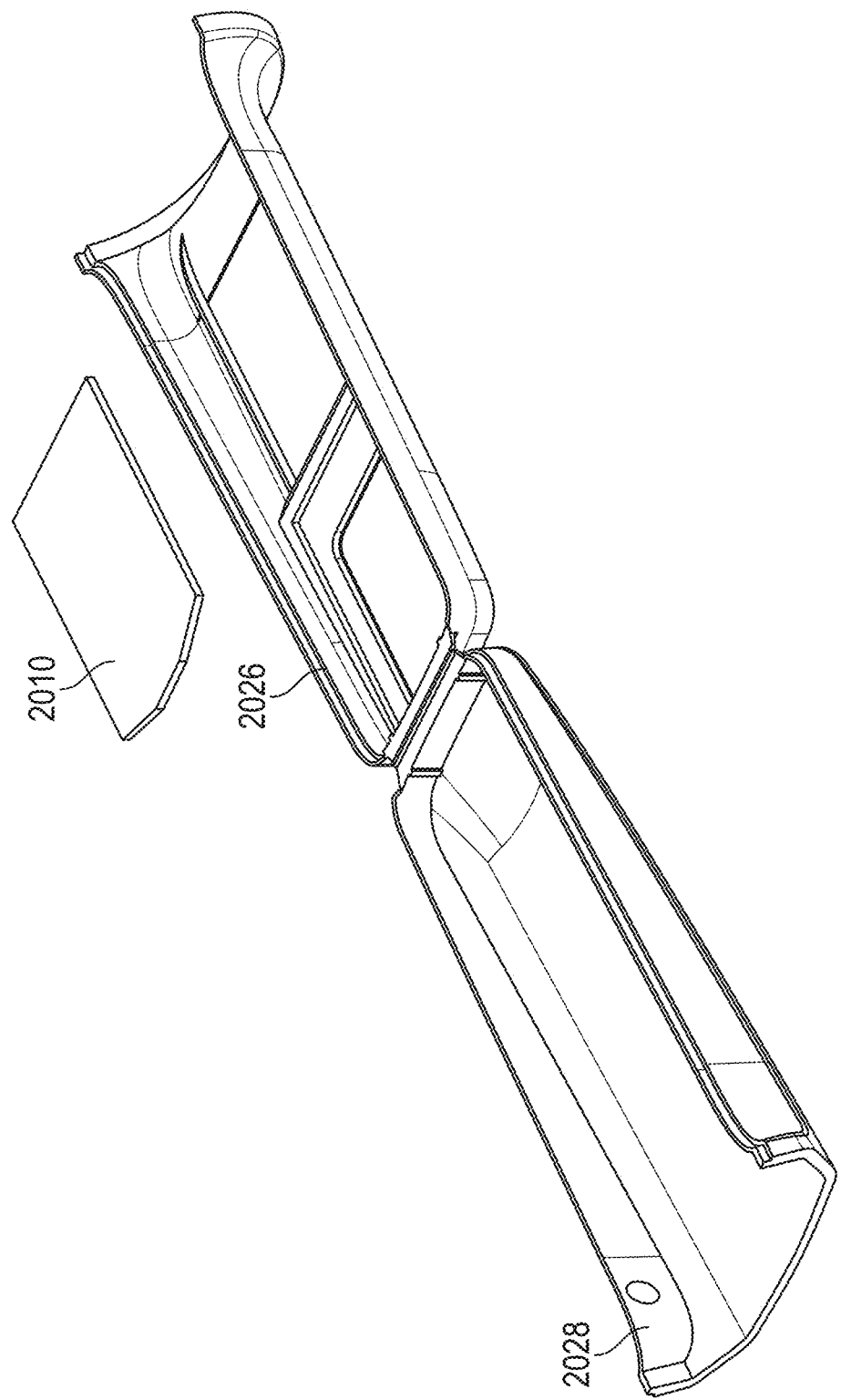

INTRAORAL SCANNER SLEEVE

CLAIM OF PRIORITY

This patent application claims priority to U.S. Provisional Patent Application No. 63/189,915, filed on May 18, 2021, titled "INTRAORAL SCANNER SLEEVE" and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein may relate to protective sleeves for optical scanners, and particularly for intraoral scanner that may be useful in scanning the intraoral cavity.

BACKGROUND

Many dental and orthodontic procedures can benefit from accurate imaging (including, but not limited to accurate three-dimensional, 3D, imaging, 2D imaging, surface scanning, florescent scanning, etc.) to provide digital descriptions of a patient's dentation and intraoral cavity. An intraoral scanner may provide such imaging. Typically an intraoral scanner may include a hand-held sensing component for scanning within the patient's oral cavity. The hand-held component may be referred to as a wand, and may include one or more windows for transmitting and/or receiving light to form images from within the patient's oral cavity.

Because the intraoral scanners may be inserted at least partially into the patient's mouth, a protective element, referred to herein as a sleeve or as a protective sleeve, may be used with the wand. The sleeve can act as barrier between the wand and the patient to protect the patient from cross-contamination. Thus, the sleeve may be removable from the wand so that the sleeve can be replaced before using the wand with the next patient. However, it has proven difficult to manufacture sleeves that provide sufficient seal against contamination and securely couple with the wand of the intraoral scanner within acceptably high tolerances. In addition, the optical qualities and the shape and size of the sleeves may affect the performance of the intraoral scanner. For example, if the sleeve does not fit on the intraoral scanner properly or does not have good optical transmission properties, the intraoral scanner will not obtain a good scan of the patient's mouth, resulting in inaccurate scan results.

Described herein are methods and apparatuses, including protective sleeves, systems including protective sleeves, and methods of using them to address these problems and that may enhance the safety and functionality of intraoral scanners.

SUMMARY OF THE DISCLOSURE

Described herein are apparatuses, including sleeves, intraoral scanning systems to use these sleeves, and methods of using the sleeves. Generally described herein are sleeves for an intraoral scanner that are configured to securely couple with an intraoral scanner wand. These sleeves may be adapted as a unitary (single) body and may include one or more internal structures that are integrally formed with the unitary body on the inside of the sleeve to guide and direct the distal end of a wand of an intraoral scanner into the sleeve securely without risking damage to the wand of the intraoral scanner and/or the window (e.g., glass cover window) of the sleeve.

For example, described herein are sleeves (e.g., protective sleeves) for use with an intraoral scanner that include: a sleeve body configured to fit onto a wand of an intraoral scanner; a window through the sleeve body formed of a transparent material (e.g., glass or equivalent material such as a transparent plastic), wherein the window is configured to align with a field of view of the intraoral scanner. In some examples the window (e.g., glass insert) may include one or more identifiers configured to impinge into the field of view of the intraoral scanner when the sleeve is attached to the intraoral scanner. For example, the identifier may include a projection or protrusion into the window opening. The identifier may identify one or more of: the identity of the sleeve and the use status of the sleeve (e.g., sleeve is on/not on).

In general, the sleeve body may be configured to be worn over the wand, and/or attached to the end of the wand.

Also described herein are intraoral scanning systems. Any of these systems may be configured to include an intraoral scanner and one or more sleeves that are configured to be used with the intraoral scanner. For example, an intraoral scanning system may include: an intraoral scanner comprising a wand having a transmission window for transmitting and/or receiving light to form images from within the patient's oral cavity and a processor, the transmission window having field of view; and a sleeve configured to be worn on the wand, the sleeve comprising a sleeve body, a sleeve window through the sleeve body, the sleeve window configured to align with the transmission window.

Any of the sleeves described herein may include one or more internal guiding structures (e.g., ramps, slides, etc.) within the inside of the sleeve for guiding and/or securing the wand of the intraoral scanner in the sleeve to prevent damage to the wand and/or to prevent damage to the sleeve, and in particular the window (transparent, e.g., glass, cover of the sleeve) through which imaging may be performed. This internal guiding structure (e.g., ramp) may be formed integrally with (e.g., injection molded as part of) the inside of the sleeve, and of the same material as the sleeve. For example, described herein are sleeves for intraoral scanners that may include: an elongate and hollow body having a distal end and a proximal end, wherein the distal end is tapered and closed, and the proximal end is open to receive an intraoral scanner; a window opening on a lateral side of the distal end; a transparent (e.g., glass, clear plastic, etc.) cover over the window opening; and an internal guiding structure (e.g., ramp) formed integrally with the elongate and hollow body, wherein the ramp is positioned within the hollow body proximal to the window opening, and configured to guide a distal end of the intraoral scanner away from the window opening as the intraoral scanner is inserted into the sleeve.

In some examples the internal guiding structure comprises a plurality of ribs or fins extending in a proximal to distal direction within the hollow body. The ribs or fins may have a triangular shape (e.g., having a more acute angle, e.g., between 5 degrees and 45 degrees, proximally and a less acute angle, e.g., between 25 degrees and 90 degrees, distally. The internal guiding structure may be arranged within 10 cm of the window opening, on the same side of the hollow body as the window opening, and proximal to the hollow opening, so as to guide the distal end of a wand into the correct position and alignment with the window opening, for imaging through the transparent window.

Any of these apparatuses (e.g., devices, sleeves, etc.) may include a foam at least partially circumferentially around the window opening within the hollow body. The transparent cover may be secured against the foam. The form may be a compressible foam. In some variations the foam may seal the transparent window against the window opening of the sleeve.

Any of the sleeves described herein may include one or more projections from a periphery of the window into the window opening configured to impinge into a field of view of the intraoral scanner when the intraoral scanner is engaged with the sleeve. These one or more projections may be detected by the intraoral scanner, and their shape and/or position may be detected by the intraoral scanner automatically or manually to identify the identity (e.g., make, model, batch, etc.) of the sleeve and/or that the sleeve has attached over the wand; in some examples the projection or other marking on the sleeve may be detected and used to confirm that the sleeve has been correctly or fully coupled to the wand.

Any of the sleeves described herein may include an extension at the proximal end of the rigid portion of the sleeve. Thus, the sleeve's elongate and hollow body may be formed of a proximal region including a rigid or semi-rigid body. A softer, more flexible extension region may be attached and/or may extend from the proximal end of the sleeve. For example, the sleeve may include an extension extending from the proximal end of the elongate and hollow body. In some examples the sleeve extension is welded (e.g., laser welded) to the sleeve. The material forming the sleeve extension may be the same as the material of the sleeve (e.g., polyethylene). The sleeve extension may be configured to invert over itself when pulled distally, such as when removing the sleeve from over the wand. For example, the sleeve extension may prevent contamination by inverting back over itself (trapping any contaminated portions within the sleeve).

As mentioned, in any of these examples the sleeve may be formed of a polymeric material, such as, for example, a polyethylene material.

Any of these sleeves may include an adhesive seal around the window opening sealing the transparent cover to the window opening. The adhesive seal may be formed of a liquid adhesive that is polymerized, e.g. around the edges of the window opening, including along the transparent cover.

In some examples the sleeve includes a sealing frame coupled to an outside of the elongate and hollow body so that the transparent cover is sandwiched between a periphery of the window opening and a sealing frame window opening. The sealing frame may be formed of a different material or the same material. In some examples the sealing frame is coupled to the elongate and hollow body by a mechanical attachment, such as a friction fit, a snap fit, etc. For example, the sealing frame may be coupled to the elongate and hollow body over the window opening by one or more snap fits.

Any of these sealing frames described herein may include an adhesive channel peripherally arranged at least partially around the sealing frame window opening. An adhesive material may be applied into the channel during fabrication and allowed to polymerize to form the adhesive seal securing and sealing the transparent cover over the window opening. In any of these examples the elongate and hollow body may include a seating region configured to hold the transparent cover. In general the sealing frame may be secured flush with the outer surface of the sleeve. For example, the sealing frame may be configured to secure to the seating region so that an outer surface of the sealing frame is flush with an outer surface of the elongate and hollow body.

In some examples the sealing frame may be secured to the sleeve over and around the window opening by a weld.

In some examples the transparent cover is secured to the sleeve by one or more projections (e.g., "snaps") formed by undercutting a peripheral region of the window opening. For example, the elongate and hollow body may include a seating region configured to hold the transparent cover, further comprising a plurality of snaps projecting into the seating region from the periphery of the window opening, wherein the snaps are configured to secure the transparent cover within the searing region.

In some examples the elongate and hollow body comprises a seating region configured to hold the transparent cover, further wherein the window opening comprises a plurality of heat-press detents projecting into the window opening from the periphery of the window opening, wherein the heat-press detents are configured to secure the transparent cover within the searing region.

In some variations the elongate and hollow body of the cover is formed integrally a flattened cylinder having a tapering distal end region that is closed. Alternatively or additionally, in some examples the elongate and hollow body of the cover is formed by a single piece that folds over itself to secure closed and form the tapered, flattened cylindrical shape, referred to as a "clamshell" body. For example, the elongate and hollow body may be formed as a clamshell body having a living hinge at the distal end of the elongate and hollow body. A lateral seam on either side of the elongate and hollow body may be sealed closed. In some examples the lateral seam(s) along the sides extending from the distal end to the proximal end opening are formed with the top half is folded over and engages the bottom half; the top half and bottom half may engage with each other by a friction fit or other engagement. The seam(s) may be sealed together using an adhesive and/or by welding (e.g., laser welding) or the like.

Any of the sleeves described herein may include a flavorant. The flavorant may be any appropriate flavor, e.g., mint, cinnamon, citrus (orange, grapefruit, etc.), peppermint, chocolate, etc. The flavorant may be added to the material forming the sleeve. In some examples the flavorant is added as a coating applied to an outer surface of the cover. The flavorant may be sprayed on or dip coated, etc.

Any of the transparent windows may include one or more anti-fogging or de-fogging components, including (but not limited to) coatings or layers for anti-fogging/defogging).

The sleeves described herein may be configured to provide a seal and protection against contamination of the wand so that the same wand may be used with different patients by exchanging sterile sleeves between patients. Any of these sleeves may be configured to seal to greater than 90 kPa.

In general, the wand may be inserted into the sleeves and guided (e.g., using an internal guiding structure, e.g., ramp, or other guiding feature within the sleeve) so that the imaging sensor(s) of the wand are aligned and positioned correctly and predictably relative to the window opening and transparent cover of the sleeve. In general, the imaging window of the wand (which may be open or may include a cover, e.g., transparent wand cover) may be positioned either against the transparent cover of the sleeve or within a known tolerance of, e.g., about 0.2 mm (e.g., between 0.8 mm and 0.01 mm, between about 0.5 mm and 0.01 mm, between 0.4 mm and 0.1 mm, etc.). In particular, the internal guiding structure features described herein may be configured to position the wand in a fixed relation to the window opening and transparent cover.

As mentioned, described herein are sleeves including a sealing frame that may secure the transparent cover of the sleeve over the window opening. For example, a sleeve for an intraoral scanner may include: an elongate and hollow body having a distal end and a proximal end, wherein the distal end is tapered and closed and the proximal end is open to receive an intraoral scanner; a window opening on a lateral side of the distal end; a transparent cover over the window opening; a sealing frame coupled to an outside of the elongate and hollow body so that the transparent cover is sandwiched between a periphery of the window opening and a sealing frame window opening; and an adhesive channel peripherally at least partially around the sealing frame window opening holding an adhesive securing the transparent cover within the window opening.

In some examples, the sleeves may be formed with a living hinge, as mentioned above. For example, a sleeve for an intraoral scanner may include: an elongate and hollow body having a distal end and a proximal end, wherein the distal end is tapered and closed and the proximal end is open to receive an intraoral scanner; a window opening on a lateral side of the distal end; a transparent cover over the window opening; wherein the elongate and hollow body comprises a clamshell body having a living hinge at the distal end of the elongate and hollow body, further wherein a lateral seam on either side of the elongate and hollow body is sealed closed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 10A-10H illustrate front, back, bottom, top, left side, right side, front perspective and back perspective views, respectively, of one example of a sleeve as described herein.

In FIG. 12A a wand is shown inserted into the sleeve.

FIGS. 20A-20C illustrate assembly of a sleeve for an intraoral scanner similar to that shown in FIGS. 18A-18B and 19A-19B.

DETAILED DESCRIPTION

Figure 1:
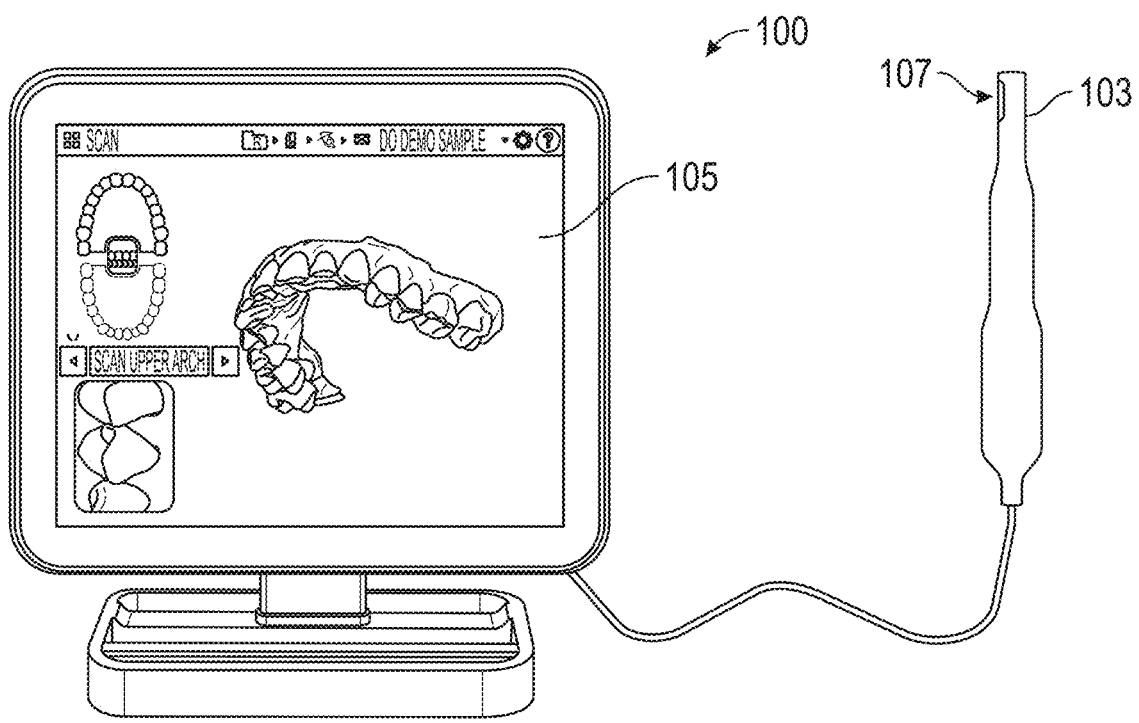
FIG. 1 is an example of one variations of an intraoral scanner as described herein.

In general, described herein are protective sleeves for use with intraoral scanners. The protective sleeves may include a body portion, which may be configured to attach to a hand-held wand portion of an intraoral scanner, and a window portion through which the intraoral scanner may transmit light and/or receive images. The window portion may be covered with a transparent cover (e.g., a glass cover, a polymeric cover, etc.). In some examples the protective sleeves ("sleeves") for intraoral scanners described herein may include one or more projections of the peripheral of the window into the field of view of an intraoral scanner when used, which may indicate that the sleeve is attached, is attached correctly, and/or may indicate the identity of the sleeve.

In some examples, the sleeve may include an internal guiding structure (e.g., a projection, ramp, slide, etc.) that may guide or direct and/or secure a wand of an intraoral scanner within the lumen of the sleeve so that the imaging region of the wand is aligned with the transparent window, but without scratching or otherwise damaging the transparent window from within the sleeve as the wand is inserted into the sleeve. The internal guiding structure (e.g., ramp) may be positioned and/or shaped so as to guide the wand into the sleeve. The projection may be integrally formed with the body of the sleeve. In general, any of the sleeves described herein may be configured for injection molding to form the sleeve as an integral (single body) piece. Also described herein are methods of inserting a wand into a sleeve using the projection (e.g., ramp) to guide the wand into position. The internal guiding structures described herein may alternatively and equivalently be referred to as internal guides or internal guide projections.

Any of the sleeves described herein may include a sleeve extension extending from the rigid or semi-rigid body of the sleeve at the distal end opening so that it may cover more of the intraoral scanner and/or handle, cord, etc. of the intraoral scanner. The sleeve extension may be more flexible than the sleeve. In some examples the material of the sleeve may be formed of the same material as the more flexible sleeve extension.

Any of the sleeves described herein may be configured so that the sleeve may be more easily assemble, including in particular attaching or coupling the transparent cover of the sleeve into the sleeve. For example, the sleeve may be configured so that the transparent cover may be added to the sleeve from outside of the sleeve rather than through the inner lumen of the sleeve. In some examples the sleeve may include a sealing frame that may be attached or otherwise coupled to an outside of the sleeve so that the transparent cover is sandwiched between a peripheral region of the window opening and a window opening of the sealing frame. Any of the sleeves described herein may include a seal, which in some examples may be formed of an adhesive sealing material, such as a polymerizing liquid adhesive sealing material that may cure to form the seal. Any of the sleeves described herein may include a channel for holding and/or guiding the seal material around the window. For example, a sealing frame may include an adhesive channel.

The sealing frames for the sleeves described herein may be configured to mate with a seating region in the body of the sleeve. In some examples the seating region may also be configured to secure the transparent cover between the sealing frame and the seating region, including in compression. In some examples the sealing frame may be coupled (e.g., attached) to the body of the sleeve (including into the seating region) by one or more attachments. The one or more attachments may be snaps (including snaps formed integrally into the body of the sleeve and/or the sealing frame), stays, screws, etc.

In some examples the sleeve includes one or more attachments (e.g., snaps, friction fits, etc.) that may be integrally formed into the body, e.g., around the periphery of the window opening through the body. The attachments may be configured to secure the transparent cover to the sleeve without requiring an additional sealing cover. The sleeve window region may include a seating region that is configured to mate with the transparent cover with a high degree of tolerance, such as with less than a 1 mm gap (less than: a 0.9 mm gap, a 0.8 mm gap, a 0.7 mm gap, a 0.6 mm gap, a 0.5 mm gap, a 0.4 mm gap, a 0.3 mm gap, a 0.2 mm gap, a 0.1 mm gap, etc.). The one or more attachments (e.g., snaps) on the periphery of the sleeve window may secure the transparent cover in the seating region of the sleeve. As mentioned, any of these sleeves may also include a seal (e.g., an adhesive seal) around the sleeve window, sealing the transparent cover over the window opening of the sleeve. As described herein are methods of assembling any of the sleeves described herein, including methods of assembling a sleeve including one or more attachments for securing the transparent cover to the sleeve.

Also described herein are sleeves for intraoral scanners in which the window through the sleeve body (at the distal end region of the sleeve) includes a seating region into which the transparent cover is secured by heat pressing the periphery of the window of the sleeve to form detents that project partially over the transparent cover. Thus, the detents may displace material from the periphery of the window of the sleeve in and over the transparent cover. As mentioned, any of these sleeves may also include a sealing material around the periphery of the window to seal the transparent cover to the perimeter of the window.

In some examples the body of the sleeve may be configured as a clamshell structure that includes a hinge region (e.g., a living hinge) so that two halves of the sleeve may be folded together (along the hinge region) and secured together to form the sleeve having an inner hollow region (e.g., lumen) into which the wand of an intraoral scanner may be inserted and aligned for imaging through the transparent cover of the sleeve. The living hinge may be on the distal end of the assembled sleeve device or it may be located on a side of the assembled sleeve. In assembling a sleeve having a living hinge region, the sleeve may be formed integrally (e.g., by injection molding, etc., as described for other types of sleeves, and may be folded back onto itself to form the assembled sleeve. In some examples, prior to folding back onto itself, the transparent window may be inserted a seating region and sealed into position. Thus, in some examples the transparent window may be inserted from the (future) inside of the sleeve. Once the transparent window is attached (and in some examples, sealed to the body of the sleeve, the sleeve body may be assembled by folding the two conjoined halves together. In some examples, a sealing material (e.g., adhesive) may be applied to secure the two halves together. In some examples the two halves may be secured together by an attachment (e.g., snap, hook, etc.). The two halves of the sleeve may be assembled together and sealed together by a laser weld or welds along the joining region of the two halves.

A protective sleeve may be configured as a rigid, semi-rigid or compliant body that may mate with a hand-held wand portion of an intraoral scanner. The body may be configured to extend over the wand; the protective sleeve may form a barrier against the transmission of contamination such as bacteria, viruses, and like. The body may be configured to act specifically as a barrier to saliva, mucus and other biological fluids. In some variations the protective sleeve, including the body of the protective sleeve, may be formed at least in part from a polymeric material, such as a silicone, latex or other polymer. The body of the sleeve may extend over the wand and/or all or some of a cord or cable. In some examples the sleeve, as mentioned above, may include an extension region for extending over handle, cord and/or cable. For example, the sleeve, including the window and body of the sleeve (also including any extension of the sleeve) may be formed of a flexible barrier material (e.g., a plastic or other polymeric material) that may provide a fluid and/or pathogen barrier.

The protective sleeve may include a window portion that is configured to align with a corresponding window on the wand to transmit light and/or other information for forming images of the patient's dental cavity. The window region may be sized and/or shaped to match or refine the imaging window of the wand. As will be described in some variations, below, the sleeve window may be sized and/or shaped so that at least a portion of the sleeve window projects or extends at least partially into the field of view of the imaging window of the wand, in order to aid in authentication and/or confirmation that the sleeve is applied, and/or is applied correctly. The sleeve window ("transparent cover") may be formed of a transparent material, and in particular may be formed of a material that is transparent to the one or more wavelength(s) used by the intraoral scanner for imaging the patient's dentition. For example, the transparent cover may be formed of an optically clear material, or a material that is transparent in the optical wavelengths and/or the fluorescent wavelength(s) being used and/or the near-infrared wavelengths. The sleeve may be formed of a material that is rigid or semi-rigid and may be a polymeric material, e.g., polycarbonate, polymethyl methacrylate (PMMA), polyethylene terephthalate (PET), amorphous copolyesters, polyvinyl chloride (PVC), liquid silicone rubber (LSR), cyclic olefin copolymers, polyethylene (PE), ionomer resin, transparent polypropylene (PP), fluorinated ethylene propylene (FEP), methyl methacrylate-acrylonitrile-butadiene-styrene (MABS, e.g., transparent ABS), polystyrene (general purpose—GPPS), styrene methyl methacrylate (SMMA), etc. The transparent cover may likewise be formed of any of these materials, and/or may be formed of glass. One or more material (including layers of materials) may be used. The sleeve window may be sealed to the body portion to perfect the barrier against biological contamination. In some variations, all or a portion of the sleeve may also be formed of the same material as the window. In some variations the sleeve may be formed of a material that is different from the window.

In general, the protective sleeve may mate with and engage the intraoral scanner. For example, the protective sleeve may be configured to cover a hand-held wand of an intraoral scanner. In some variations the protective sleeve extends over the end of the hand-held wand so that the window of the protective sleeve aligns with the imaging window of the wand. The body of the protective sleeve may extend over the hand-held wand and in some variations down the body of the wand some distance (e.g., 6 inches or more, 8 inches or more, 12 inches or more, 16 inches or more, 2 feet or more, 3 feet or more, 4 feet or more, 5 feet or more, etc.).

In some variations the protective sleeve may also be textured for gripping (e.g. by a user's hand) securely when operating the intraoral scanner. The protective sleeve may also include one or more ridges, bumps, channels, textures, etc., to assist in gripping.

A protective sleeve may comprise a housing configured to fit over a portion of an intraoral scanning device and protect the intraoral scanning device from an external environment. The intraoral scanning device (e.g., wand) may comprise a first aperture (e.g., opening) for transmission of optical signals, and the sleeve may include a second aperture (the sleeve window which is typically covered by a transparent cover) for transmission of the optical signals. The second aperture may be aligned with the first aperture when the wand is inserted into the sleeve housing. The protective sleeve may be configured so that when the wand is inserted into the sleeve, the transparent cover is aligned with a defogging element of the wand of the intraoral scanner. For example, an external surface of the transparent cover may receive heat generated by a defogging element to prevent fogging of the transparent element. In some examples the transparent cover may be adapted for defogging (e.g., including a coating of an anti-fogging/defogging coating, thermally conductive coating(s), etc.).

The sleeves described herein may be referred to as protective sleeves. The sleeves may include additional materials and components, including lighting (e.g., one or more LEDs), sensors, circuitry, or the like, which may be embedded and/or held within the protective sleeves.

FIG. 1 illustrates one example of an intraoral scanner as described herein, including a wand 103. One example of an intraoral scanner 100 is the iTero® intraoral digital scanner manufactured by Align Technology, Inc. In general, an intraoral scanner may include a hand-held wand 103, which may include an optical system (including projection/imaging optics) comprising one or more lenses and having an optical axis. The apparatus may also include illumination optics. The apparatus can comprise an axial scanner (e.g., a depth scanning module) that is configured to be move the projection/imaging optics system along the optical axis. The apparatus may include a beam splitter configured to transmit light from the light source (after passing through the pattern) to the object and reflect light returning from the object onto an imaging sensor. Thus, the apparatus may include an image sensor configured to receive light returning from the object (via the projection/imaging optics) through the beam splitter. The apparatus can be configured for 3D scanning to at least a portion of the object, for example, intraoral dental 3D scanning for all derivatives of dental restorative and orthodontics indications. The apparatuses for confocal scanning disclosed here can include a confocal illuminator. The optical system may include a projection/imaging system or subsystem including projection optics and imaging optics. For example, the projection optics and the imaging optics can be configured to share the same optical elements (lenses) and the same optical path. The apparatus can comprise the depth scanning module, which comprise a compact linear actuator, for example, a voice coil motor (VCM). The scanner can comprise a front tip, which can include a 45-degree (e.g., back-heated defogging) fold mirror.

The scanner may include one or more processors and may include on ore more illumination sources (LEDs, lasers, etc.). In FIG. 1, the hand-held wand 103 also include a window 107 providing optical access into the scanner. The window may include an optically transparent cover. The scanner may be wireless or wired to additional components of the system, including one or more additional processors. The scanner may generally illuminate and/or image in the visible spectrum, in the infrared or near-infrared spectrum, in the florescence spectrum, etc. A display 105 may also be included as part of the system. The intraoral scanner shown in FIG. 1 may be used with one or more sleeves, as shown in FIGS. 2 and 3.

Figure 2A:
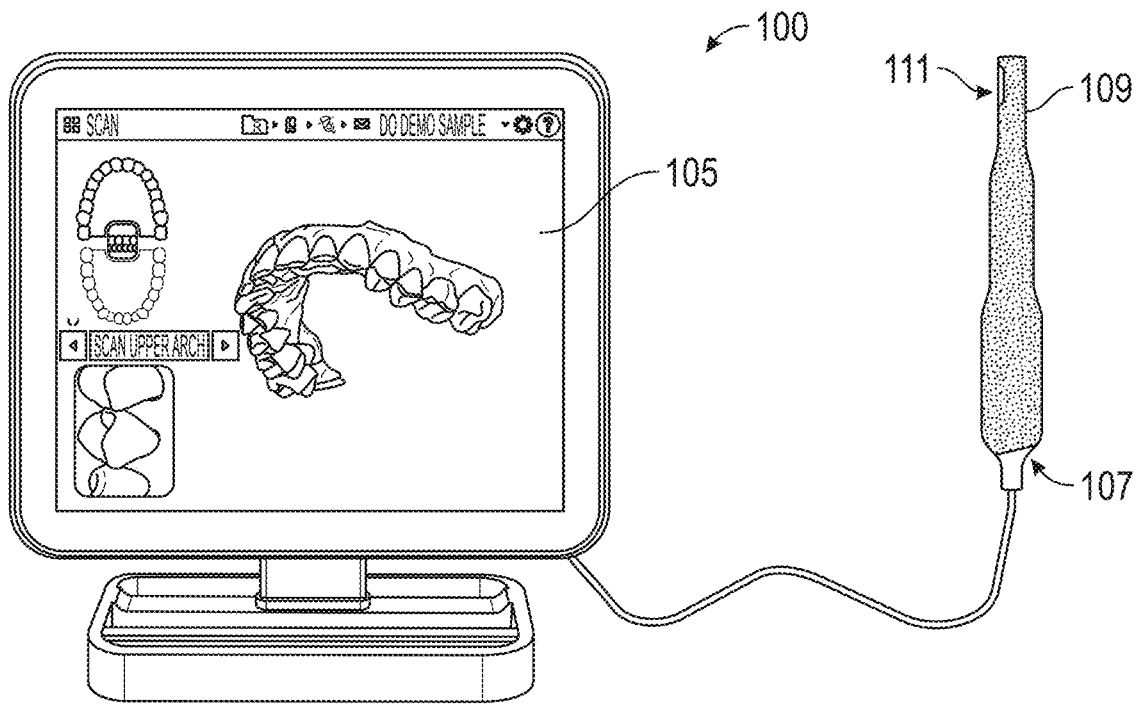
FIG. 2A illustrates the use of a protective sleeve with the example of the intraoral scanner as described herein.
Figure 2B:
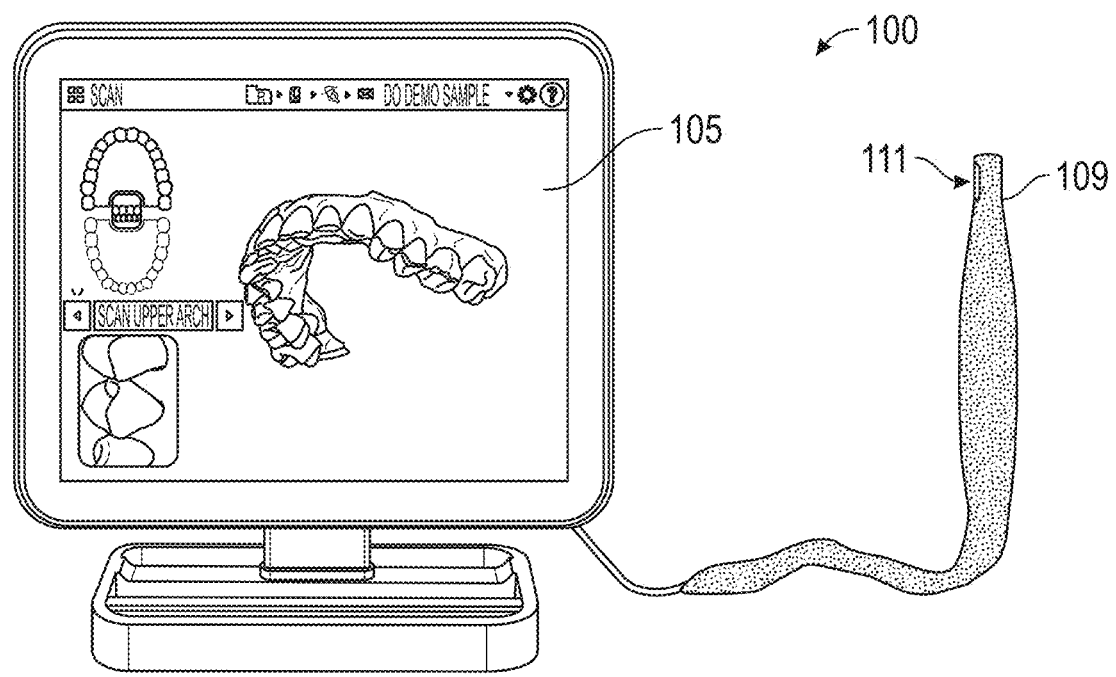
FIG. 2B illustrates the use of another example of a protective sleeve with an intraoral scanner as described herein.

In FIG. 2A, the intraoral scanner 100 includes a protective sleeve 109 that is placed over the hand-held wand 103, so that a sleeve window 111 is aligned with the window in the scanner 107 (not visible in FIG. 2A). FIG. 2B shows an alternative variation in which the sleeve 109 is longer, extending over the wand and connecting cable. Thus, the sleeve shown in FIG. 2B includes a sleeve extension; the distal end of the sleeve (the sleeve body) may be formed to have a more rigid or semi-rigid body, while the more proximal end extending from this sleeve body may be more flexible. In some examples the sleeve body is formed from the same material (e.g., poly a polyethylene material) as the sleeve extension; the two regions may be laser welded together. The difference in rigidity of these regions may depend on the thickness of the material.

Figures 3A, 3B:
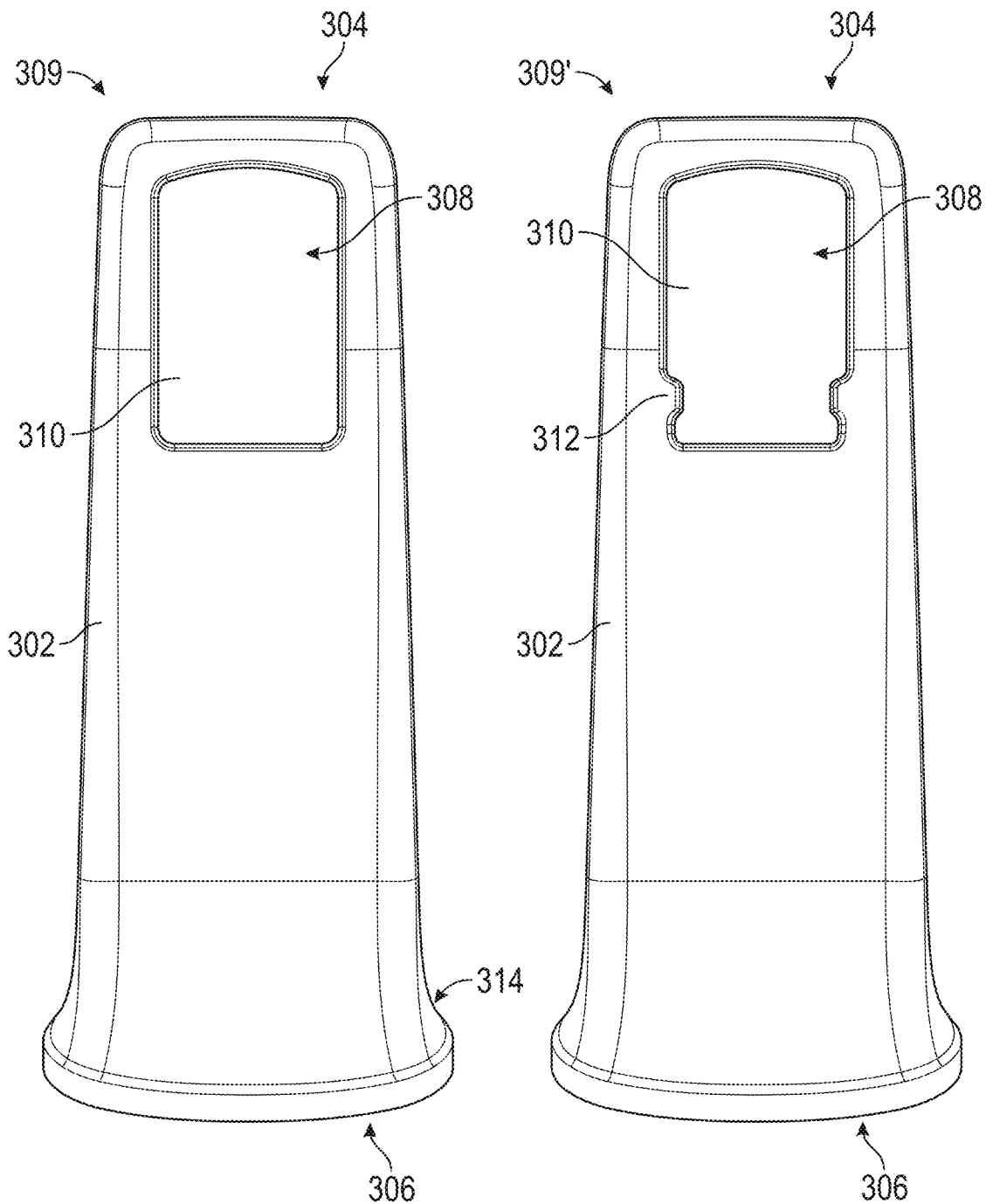
FIG. 3A illustrates one example of a protective sleeve for an intraoral scanner.
FIG. 3B shows another example of a protective sleeve for an intraoral scanner as described herein.

FIGS. 3A-3B illustrate two examples of protective sleeves 309, 309' as described herein. FIG. 3A shows the sleeve body 302, which may be an elongate and hollow body having a distal end 304 and a proximal end 306, wherein the very distal end (of the distal end region) is tapered and closed, and the proximal end is open to receive an intraoral scanner wand. The sleeve also includes a window opening 308 that is covered by a transparent cover 310. The base (the proximal end) of the sleeve body in this example is flared outwards 314.

FIG. 3B shows another example of a sleeve that is very similar to that shown in FIG. 3A but includes a pair of protruding regions 312 at the window periphery, which project slightly into the field of view of a wand that is inserted into the inner hollow body of the sleeve.

Figure 4:
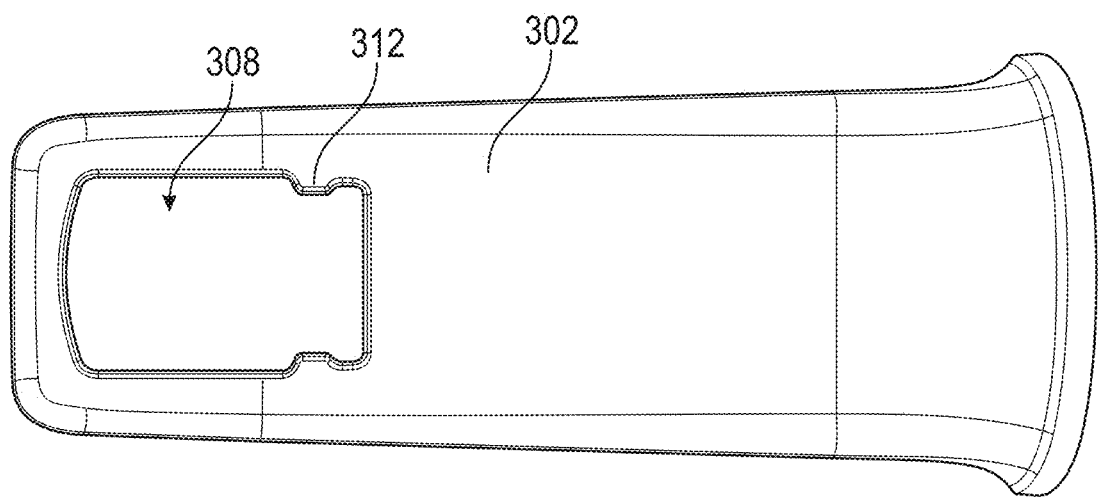
FIG. 4 is a front view of another example of a sleeve for an intraoral scanner, including a pair of projections from the periphery of the window of the intraoral scanner into the field of view.
Figure 5:
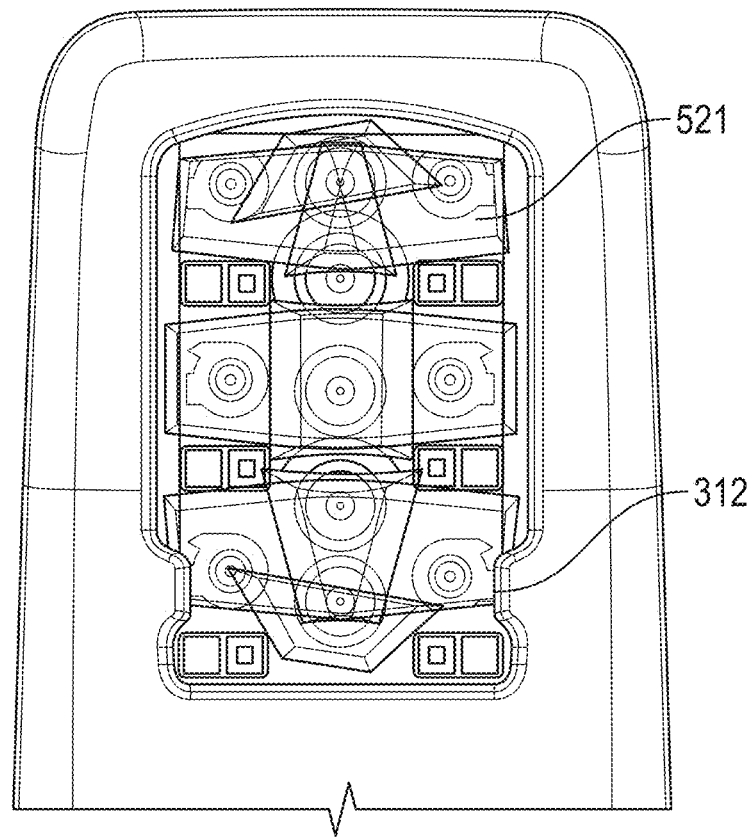
FIG. 5 is a front view of the distal end region, showing the window, of the sleeve of FIG. 6 with a wand of an intraoral scanner inserted and visible through the window.

Thus, any of the sleeves may include a notch, protrusion (e.g., bumps, projections, etc.) on the sleeve window, such as the periphery of the sleeve window, that may be within the field of view of the intraoral scanner when the sleeve is attached and may be detected by the intraoral scanner. In FIG. 3B the protrusion is formed of the window of the sleeve itself in an area that is exposed to the camera, as shown in FIGS. 4 and 5. In this example, the protrusions 312 on the edges of the opening of the sleeve window 308. The region just next to the protrusions may include opening through which one or more light sources (e.g., LEDs) in the wand may project light for scanning. In FIG. 5 the projections 312 are shown extending from the edge of the window into the field of view of the camera(s) in the wand 521, when the wand is inserted into the sleeve as shown.

As mentioned, the sleeves described herein may be fabricated as a single unitary device, to which (in some examples) the transparent cover may be added. Alternatively, in some examples the material of the entire sleeve may be transparent, and the transparent cover may be integrated (and integrally formed) with the rest of the body of the sleeve. In some examples, the body of the sleeve is formed of a polymeric material such as PE (Polyethylene) or materials that include PE with other materials. For example, the sleeve may be formed of a mixture of HDPE and LDPE (e.g., between 60-95% HDPE and between 5-40% LDPE). The PE may be laser welded as described herein to secure, e.g., the extension region.

As mentioned above, any of the sleeves described herein may include one or more internal (within the hollow cavity of the sleeve) guiding structures, such as ramps, to guide and/or lock (e.g., releasably lock) the wand in position so that it is aligned and/or secured within the sleeve. Any of these internal guiding structures may also be retainers that retain (releasably retain) the wand within the sleeve and prevent it from moving substantially within the sleeve, which may miss-align the wand imaging optics and the transparent cover (or window) of the sleeve.

Figure 6A:
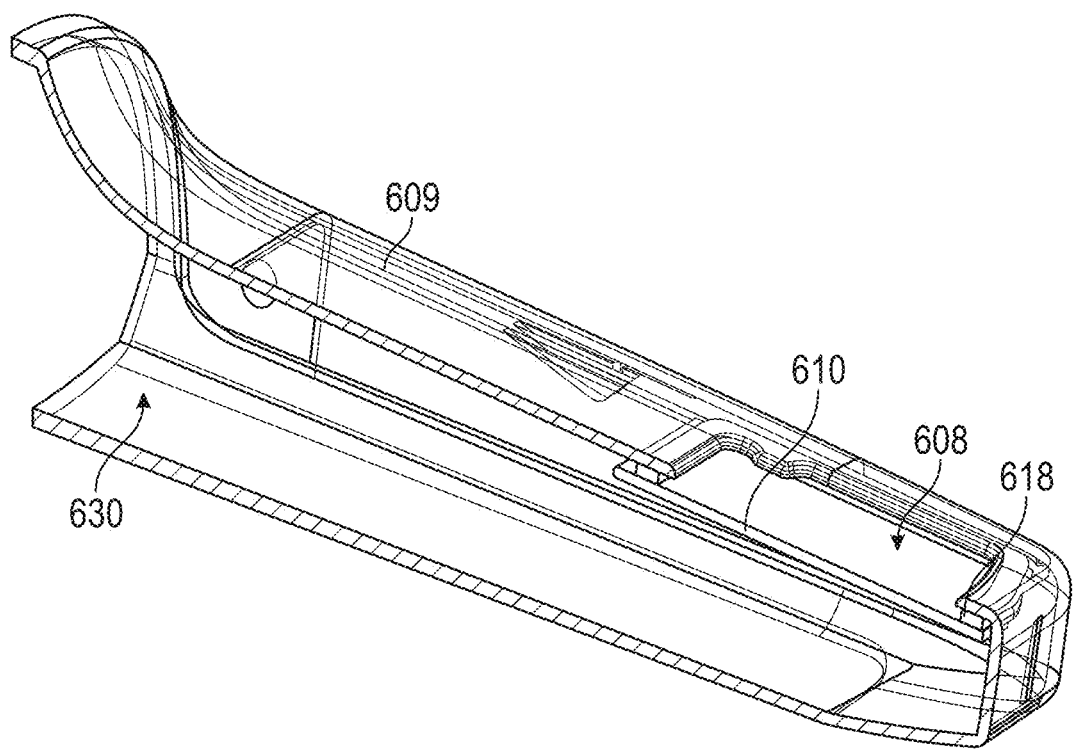
FIGS. 6A and 6B show examples of top perspective section and bottom perspective section views of one example of a protective sleeve including an integral internal guiding structure (e.g., ramp) as described herein.
Figure 6B:
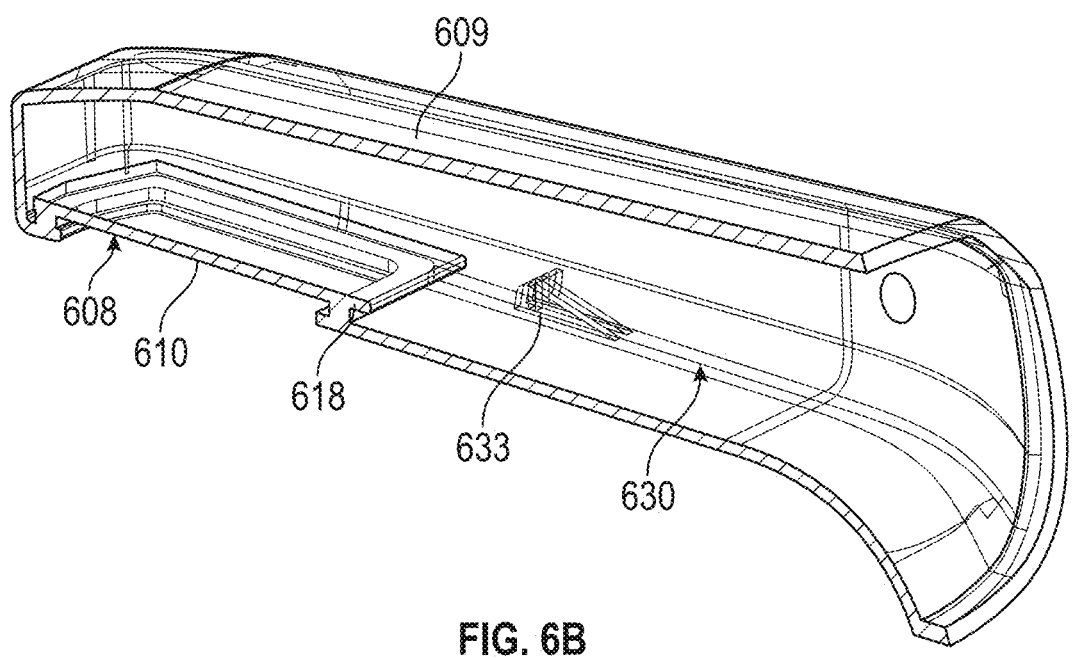

In some examples the internal guiding structure is formed integrally (as a single piece, e.g., as by injection molding) with the body of the sleeve. For example, the internal guiding structure may be configured as a ramp that is positioned just proximal (e.g., within about 1 cm, within about 2 cm, within about 3 cm, within about 4 cm, within about 5 cm, within about 6 cm, within about 7 cm, within about 8 cm, within about 9 cm, within about 10 cm, etc.) to the window opening region of the sleeve, on the internal surface of the sleeve. In some examples the internal guiding structure is a ramp formed of a plurality of triangular ribs or wings that extend from the inside of the sleeve body. For example, FIGS. 6A and 6B illustrate cross-sections of an example of a sleeve similar to those shown in FIGS. 3A-3B. FIG. 6B shows the inside 630 of the sleeve 609 including an internal guiding structure 633 configured as a ramp or slide. In this example, only a single ramp/slide is shown; additional ramps/slides may be positioned adjacent to the window (in the half of the sleeve not shown in FIG. 6B for example).

The internal guiding structure (e.g., ramp or slide) may generally have a surface that extends from the inner wall of the sleeve up above the height of the window region relative to the inter wall, which may guide the wand and prevent it from scraping or scratching the inside of the window region 608 of the sleeve (e.g., the transparent cover in variations including a transparent cover).

Figure 6C:
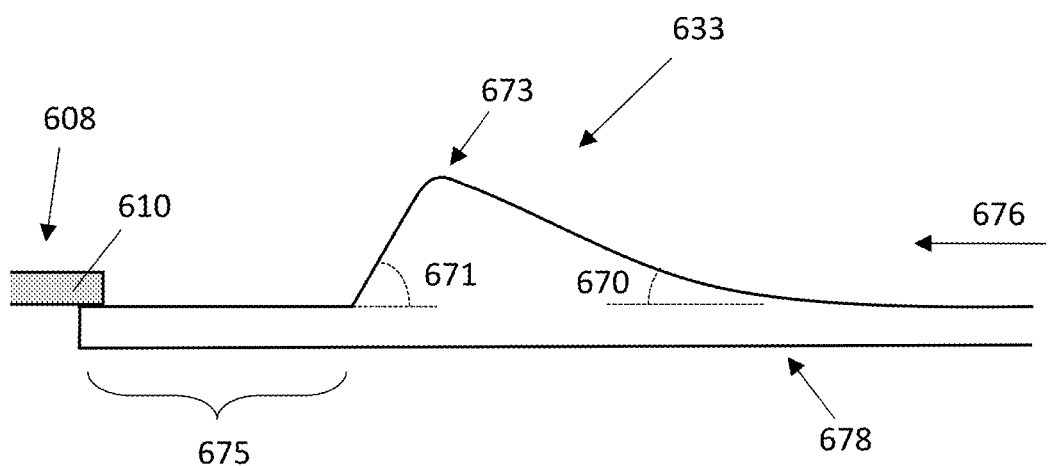
FIGS. 6C-6E schematically illustrate cross-sections through examples of internal guiding structures as described herein.
Figure 6D:
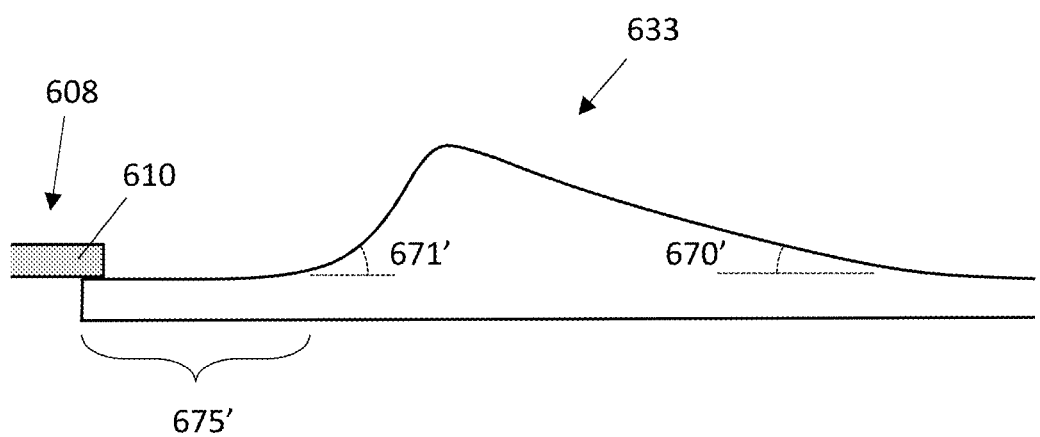
Figure 6E:
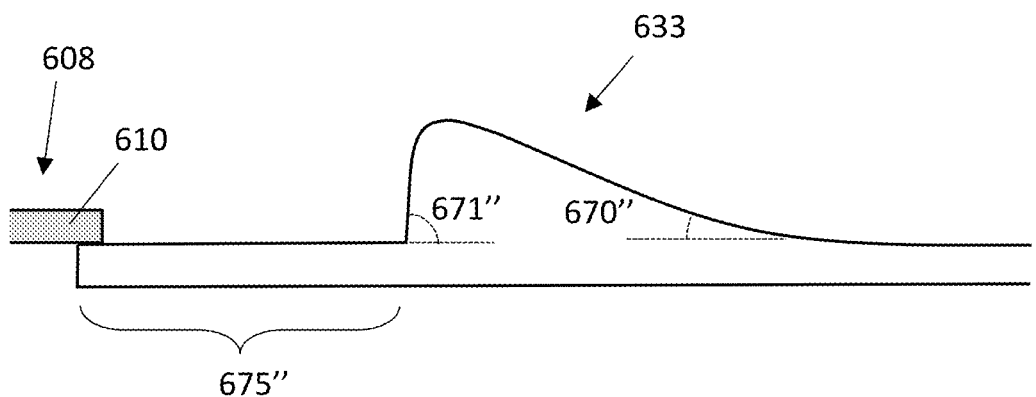

FIGS. 6C-6E illustrate examples of internal guiding structure (e.g., ramps) that may be used, shown in cross-section. For example, in FIG. 6C the internal guiding structure has an approximately triangular cross-section for guiding a wand into the hollow distal end of the sleeve. As the wand is slid distally 678, it may be guided by the ramp distal face to side up, away from the edge of the window 608. In this example the distal face has an angle 670, 670', 670" relative to the wall of the cover from which it is formed (and extends into the inner hollow of the sleeve) that may be between about 10 degrees and about 50 degrees (e.g., between about 10 degrees and about 45 degrees, between about 10 degrees and 40 degrees, between about 15 degrees and 50 degrees, etc.). The ramp is offset a distance 675 from the window opening 608 and thus the transparent cover 610. The opposite side of the ramp may also be curved and form a ramp face that may help remove the wand from the sleeve back over the ramp; in some variations this second, proximal-facing ramp may be angled relative to the wall of the cover from which the ramp is formed with a greater angle than the distal-facing ramp. For example the angle 671, 671', 671" of the proximal-facing ramp may be between about 15 and about 90 degrees. Either or both the distal-facing ramp and the proximal-facing ramp may have a continuous (e.g., smooth) curve as shown in FIGS. 6A-6D. In FIG. 6E the proximal-facing ramp is an abrupt transition (having a 90-degree angle). The spacing (offset distance) 675, 675', 675" between the ramp and the window opening may be, e.g., between about 1 mm and about 2 cm (e.g., between 1 mm and 1 cm, between 1 mm and 9 mm, etc.). In some examples the internal guiding structure is not offset from the edge of the window region 608, but may be immediately adjacent to it. In each of the examples of internal guiding structure shown in FIGS. 6C-6E, the internal guiding structure is a ramp having a triangular cross-section in which the top of the ramp is shown with a curved corner 673. This corner may be rounded (as shown) or sharp. In some examples the top is flattened. For example the internal guiding structure may have a trapezoidal shape (which may have sharp or rounded edges). The examples of internal guiding structures shown in FIGS. 6C-6E are also shown with sleeves in which the transparent cover 610 of the window region 608 is shown schematically on the inside of the cover. Alternatively, as will be described in greater detail below, the transparent cover may be on the outside surface 678 or may be flush (e.g., within a seating region) of the window region.

As described above, the internal guiding structure 633 may comprise a plurality of fins, as shown in FIG. 6B. In this example, the internal guiding structure includes two thin fin-like lengths extending in the proximal-to-distal direction within the inside of the sleeve and having a triangular longitudinal cross-section. In some examples the proximal-facing side of each ramp may be connected to a surface that extends between the fins (forming a proximal-facing surface). This proximal-facing surface may be optional; in some examples the internal guiding structure is formed of an arrangement of spaced apart (e.g., by 0.1 mm, 0.2 mm, 0.3 mm, 0.4 mm, 0.5 mm, 0.7 mm, 0.8 mm, 1 mm, 1.1 mm, 1.2 mm, etc., between 0.1 mm and 3 mm, between 0.1 mm and 2 mm, between 0.1 mm and 1.5 mm, between 0.1 mm and 1 mm, etc.) the fins extending from the inner wall of the body of the sleeve. Any number of fins (e.g., 1, 2, 3, 4, 5, 6, 7, 8, etc.) may be used for each internal guiding structure.

In some examples the transparent cover is attached on the inside of the sleeve, as shown in FIG. 6A. In this example, the transparent cover 610 forming a portion of the window region 608 is sealed to the periphery of the window region by a foam (window foam) material. The foam may be, for example, MED 5696R Adhesive foam (e.g., Avery Dennison) or MED 2123R adhesive (Vancive Medical Technologies). The foam may be compressible and may adhesively secure the transparent cover to the body of the sleeve. Some examples of the sleeves described herein do not include foam. In some examples an elastic material may be used instead of foam. The elastic material may be an adhesive that can be applied as a liquid or gel (or paste) but that cures into a solid, forming a seal between the body of the sleeve and the transparent cover.

In use, the cover may be applied over the distal end of a wand, for example by sliding the wand into the cover or by sliding the cover over the wand, or some combination. The wand of the intraoral scanner may slide within the hollow inner region of the sleeve and the internal guiding structure (ramp) may deflect the distal tip up and away from the transparent window (e.g., in some examples the transparent cover of the window) which may protect the transparent window and allow the wand to be positioned optimally relative to the sleeve. For example, FIGS. 7A-7B illustrate one method of attaching a cover 709 to a wand of an intraoral scanner 703.

Figure 7A:
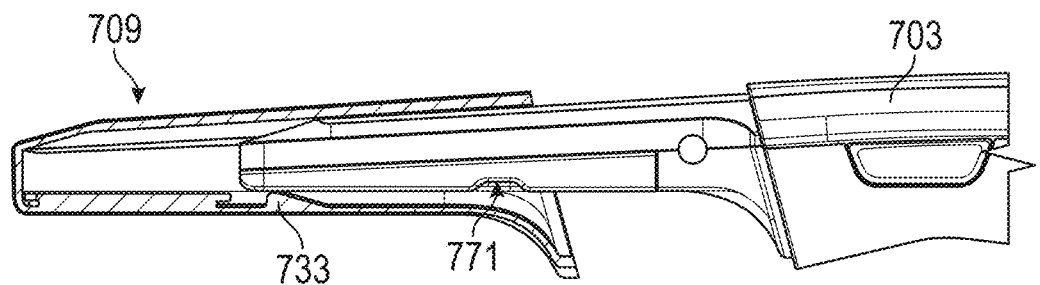
FIGS. 7A and 7B illustrate insertion of a wand of an intraoral scanner into a sleeve including in integrated internal guiding structure as described herein.
Figure 7B:
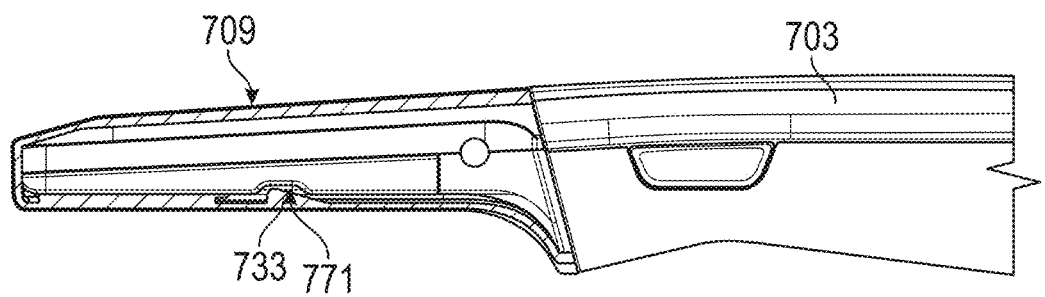

In FIG. 7A, the distal end of the wand is inserted into the distal end opening of the sleeve, and advanced to the internal guiding structure (e.g., ramp or slide 70). The internal guiding structure guides the tip of the wand above the window region and may act as a securement to reliably hold the wand in position, as shown in FIG. 7B. As shown in FIGS. 7A and 7B the wand includes an engagement region 771 for engaging the internal guiding structure. The engagement region in the body of the wand in FIG. 7 is shown as a recessed region or opening that includes surfaces that may engage with the internal guiding structure; once the wand is positioned distally far enough into the sleeve, the internal guiding structure may fit into the engagement region of the wand, allowing the tip of the wand, including the imaging window of the wand, to be aligned with the window region of the sleeve in a fixed position. The engagement region may also engage releasably hold the wand in this position relative to the sleeve until the sleeve is withdrawn proximally. In the example shown in FIG. 7, when the wand is fully extended distally the imaging window of the wand may push down against the window region, which may include a foam material, as described above, which may be compressed. The wand of the intraoral scanner may be disengaged from the internal guiding structure by pulling the wand proximally (and/or the sleeve distally) with sufficient force so that the sidewall of the engagement region slides along the proximal-facing side of the internal guiding structure, driving the wand up, away from the window region of the sleeve, and allowing it to be withdrawn out of the sleeve.

Figure 8:
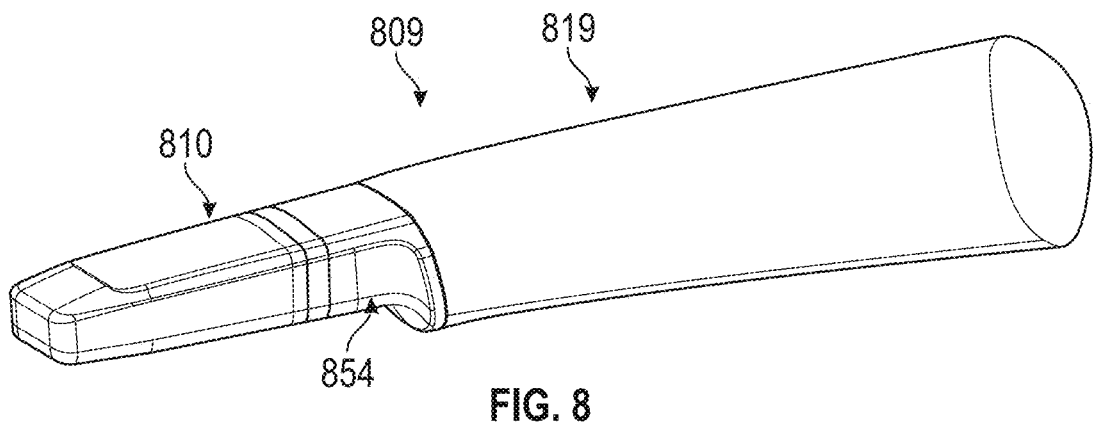
FIG. 8 is an example of a sleeve include a sleeve extension for use with a wand of an intraoral scanner as described herein.
Figure 9:
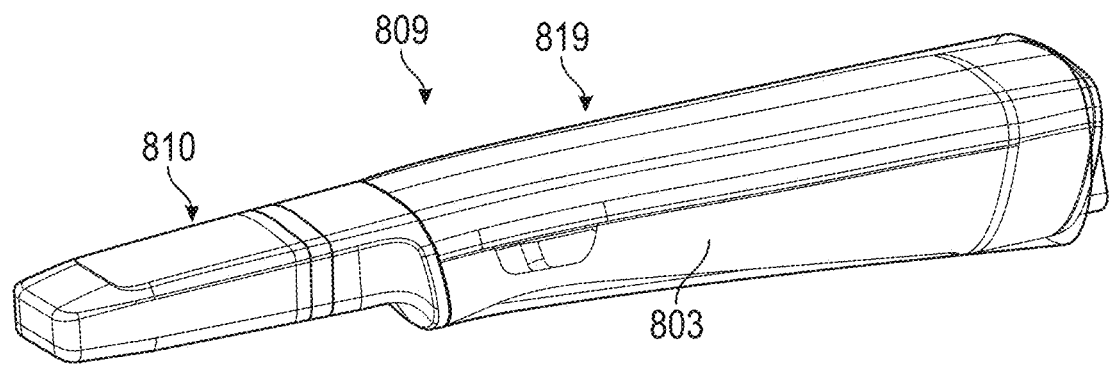
FIG. 9 is an example of the sleeve of FIG. 8 with a wand of an intraoral scanner inserted into the sleeve.
Figure 10E:
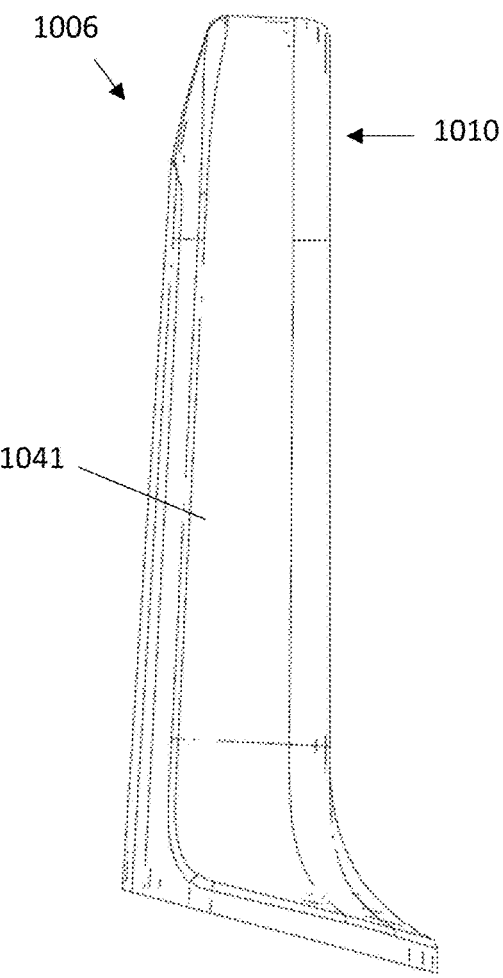
Figure 10F:
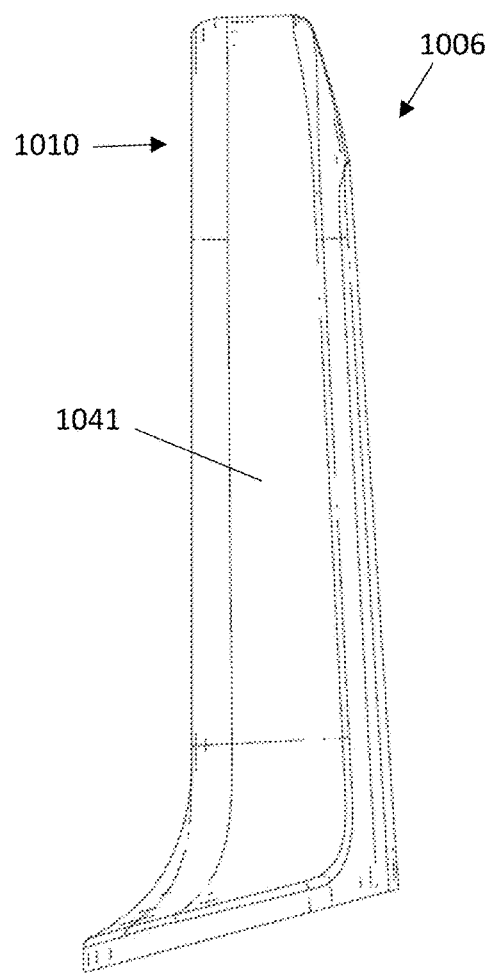
Figure 10G:
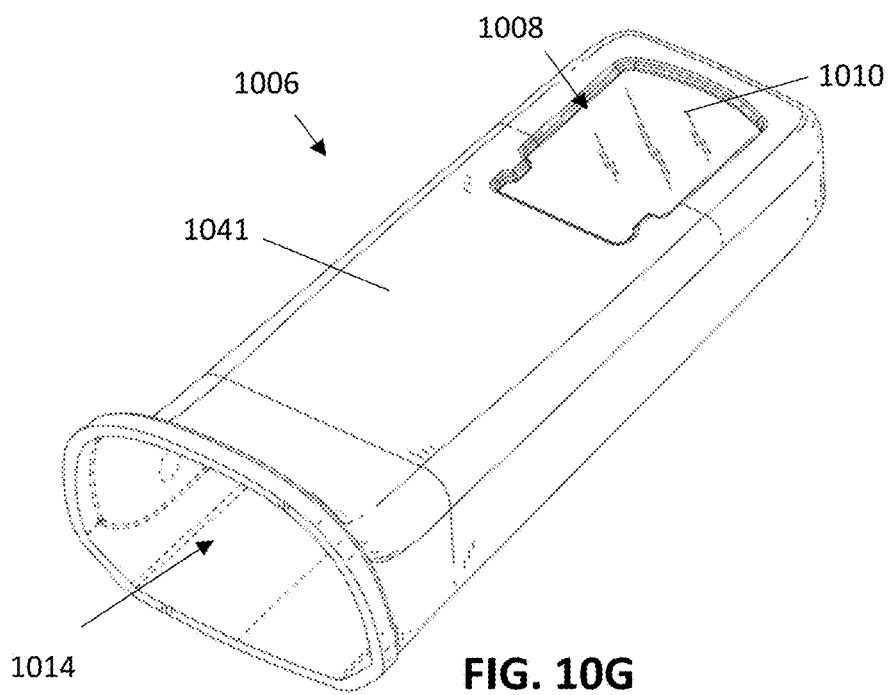
Figure 10H:
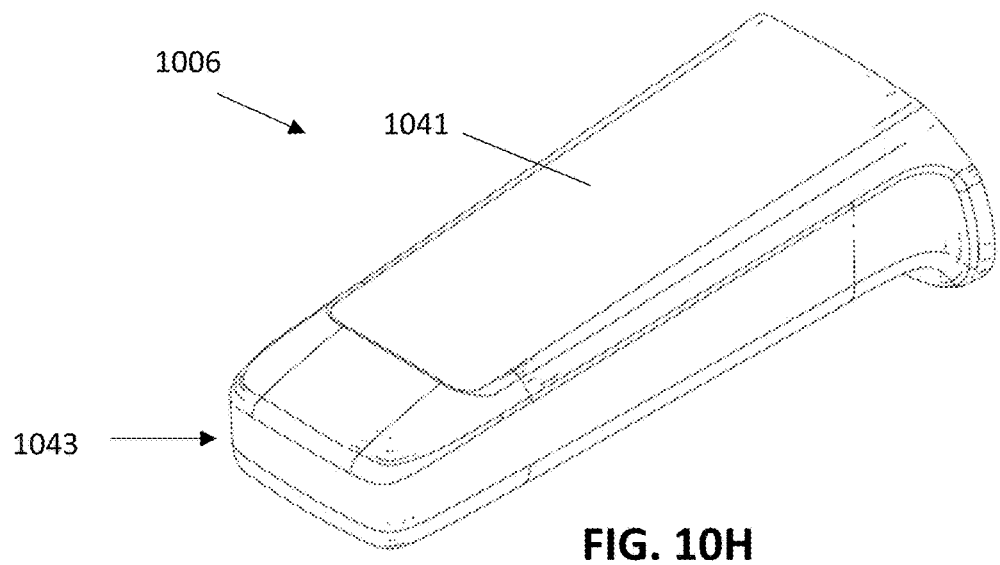

Any of the sleeves described herein may include a sleeve extension portion that extend proximally from the more rigid (or semi-rigid) proximal end, as shown in the examples of FIGS. 8 and 9. In FIG. 8 the sleeve 809 includes a more rigid distal sleeve portion 810 and a more flexible proximal sleeve extension portion 819. The proximal sleeve portion may be attached to the distal sleeve by an adhesive or a weld. In some examples the sleeve extension is welded (e.g., laser welded) 854 to the sleeve (the distal portion of the sleeve). The material forming the sleeve extension may be the same as the material of the distal portion of the sleeve (e.g., polyethylene or a mixture of polyethylene and other polymers or other forms of polyethylene). The sleeve extension may be configured to invert over itself when pulled distally, such as when removing the sleeve from over the wand.

FIG. 9 shows an example of the sleeve of FIG. 8 applied over a wand 803 of an intraoral scanner. The sleeve extension may extend for between 5 inches and 5 feet from the distal sleeve portion (e.g., between 6 inches and 4 feet, etc.). The sleeve extension may be configured to roll up over itself for removal, so as to trap any contamination on the outer surface of the sleeve within the rolled-up portion. Thus, in some examples the sleeve extension be tapered with a wider proximal end than the distal region coupled to the distal (more rigid) sleeve region. In some examples the sleeve extension may be biased (pre-rolled) back over itself. For example, a new and clean sleeve may include a rolled-up sleeve extension that may be rolled out proximally when applied over the wand. The rolled-up sleeve may be rolled so that the more distal portion is rolled within the more proximal portion. Once rolled out the sleeve extension may remain unrolled during use (and is some examples may include a fastener, such as an adhesive and/or tie, to remain unrolled and applied over the wand or cord of the wand) until it is removed. The sleeve extension may therefore be biased to roll back up to the original configuration.

FIGS. 10A-10H illustrate outer views of one example of a sleeve; as in any of the sleeves descried and illustrated herein, a sleeve extension region may be included, but not shown. The example sleeve in FIGS. 10A-10H is similar to the sleeve shown in FIG. 3B. The sleeve in FIGS. 10A-10H may include an elongate and hollow body 1041 having a distal end and a proximal end. As mentioned, the body may be rigid or semi-rigid. This body may also be referred to as the distal sleeve region in any of the sleeves described herein. The distal end of the sleeve 1043 is tapered and closed. The taper is rounded, as shown, and is compressed down so that a section through the distal end region forms a squrcle (a rounded square or rectangle) and/or ovoid cross-section, as shown in the bottom and top views of FIGS. 10C and 10D, respectively, as well as the side views of FIGS. 10E and 10F. The proximal end is opened 1014 to receive an intraoral scanner. As mentioned, (and not shown in FIGS. 10A-10H), a flexible sleeve extension may be attached to the proximal end of the more rigid distal sleeve.

The sleeve of FIGS. 10A-10H also includes a window opening 1008 on a lateral side of the distal end region. In the example shown in FIGS. 10A-10H the sleeve includes a transparent cover 1010 over the window opening.

Figure 11A:
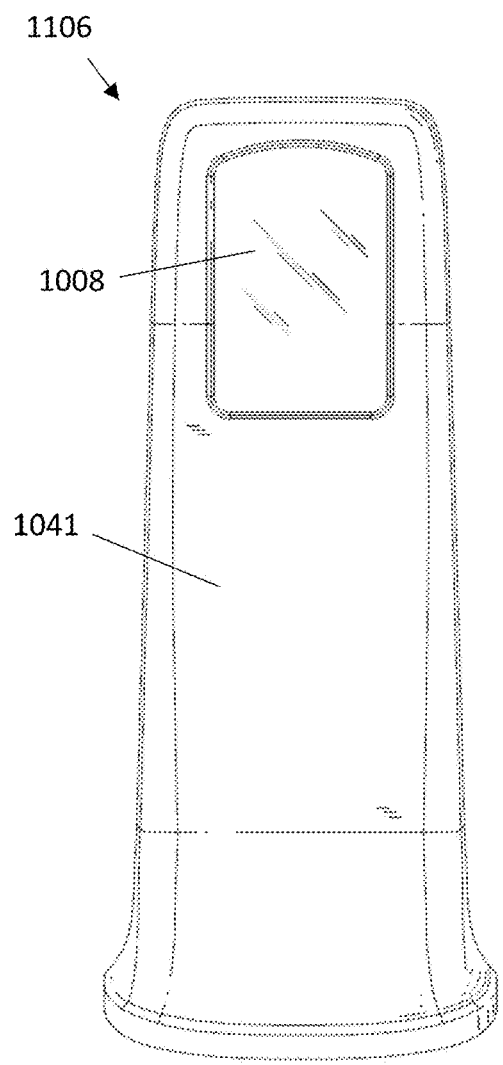
FIGS. 11A-11B show front and back views, respectively, of an example of a sleeve as described herein.
Figure 11B:
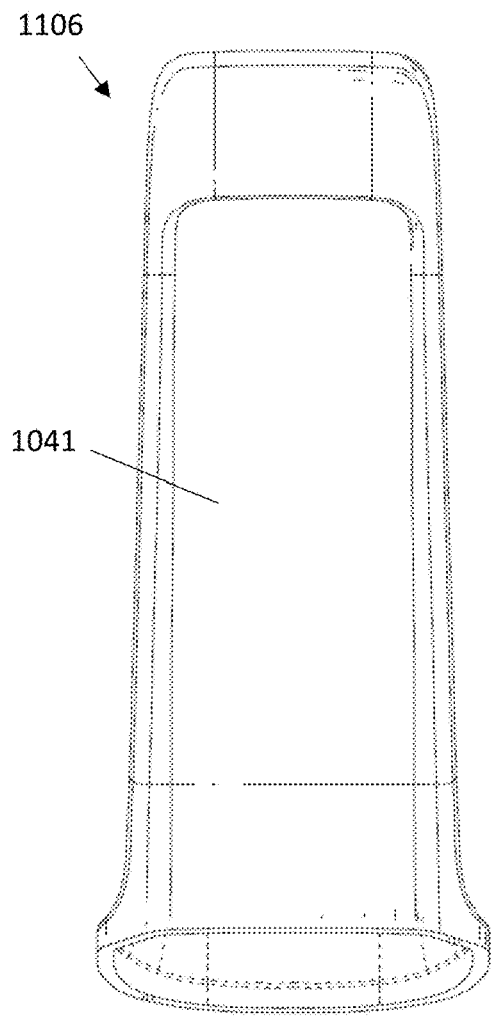
Figure 11C:
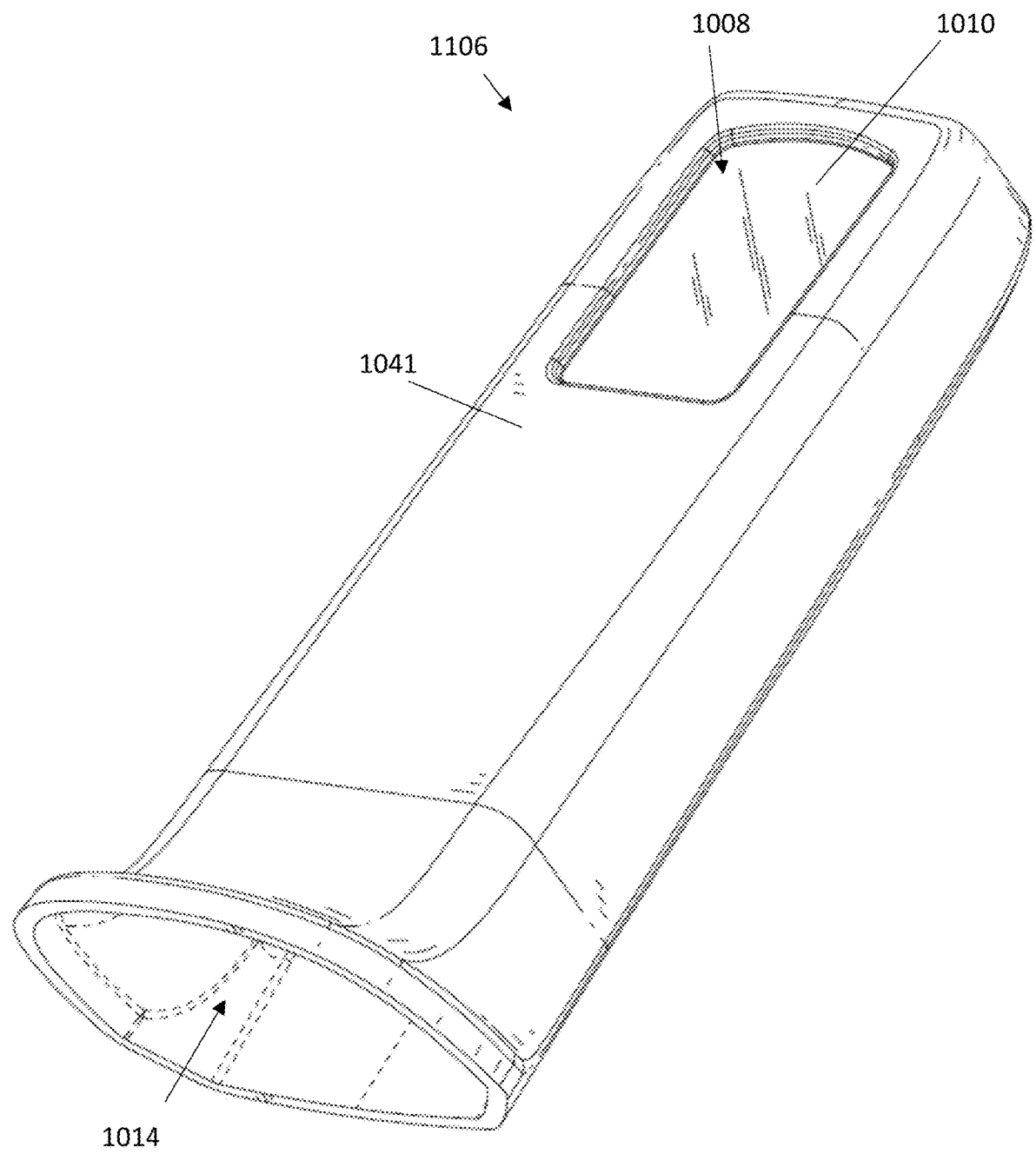
FIG. 11C shows a front perspective view of a sleeve as described herein.

FIGS. 11A-11C illustrate another example 1106 of a sleeve similar to that shown in FIG. 3A, described above.

The example shown in FIGS. 11A-11C has the same side views, top view and bottom views, and back view as the example shown in FIGS. 10A-10H.

Any of the sleeves described herein may also or alternatively a transparent cover (e.g., window) that is installed from (and in some examples onto) the outside of the sleeve. Fabrication of sleeves in which the transparent window may be installed from the outside of the sleeve rather than the inside may be much easier and less expensive as compared to mounting the transparent cover from the inside (or on an inside surface). Some of the sleeve examples described herein may be molded (e.g., by molding, extruding, etc.) with a window opening formed in the device. The transparent cover may then be mounted to the sleeve from the outer surface.

Any of the devices described herein may include a receiving area in the distal region of the body of the sleeve around the window opening of the sleeve. The receiving area may be a transparent cover (e.g., window) receiving area that may seat and secure the transparent cover. The receiving area may be configured to seat the transparent cover in a particular orientation; for example, the receiving area may include a recessed region (recessed from the outer surface of the sleeve) that may include a lip or edge around the window opening through the sleeve on which the transparent cover may sit. In some examples the receiving area may include a channel or passage on or adjacent to the seating lip or edge for holding a sealing material, including a liquid or gel adhesive material that may polymerize into the seal. Any of the receiving areas described herein may include one or more fasteners for securing the transparent cover in the seating area. In some examples the seating area may be recessed into the body of the sleeve, as described; alternatively or additionally the seating area may extend proud of the body of the sleeve.

Figure 12A:
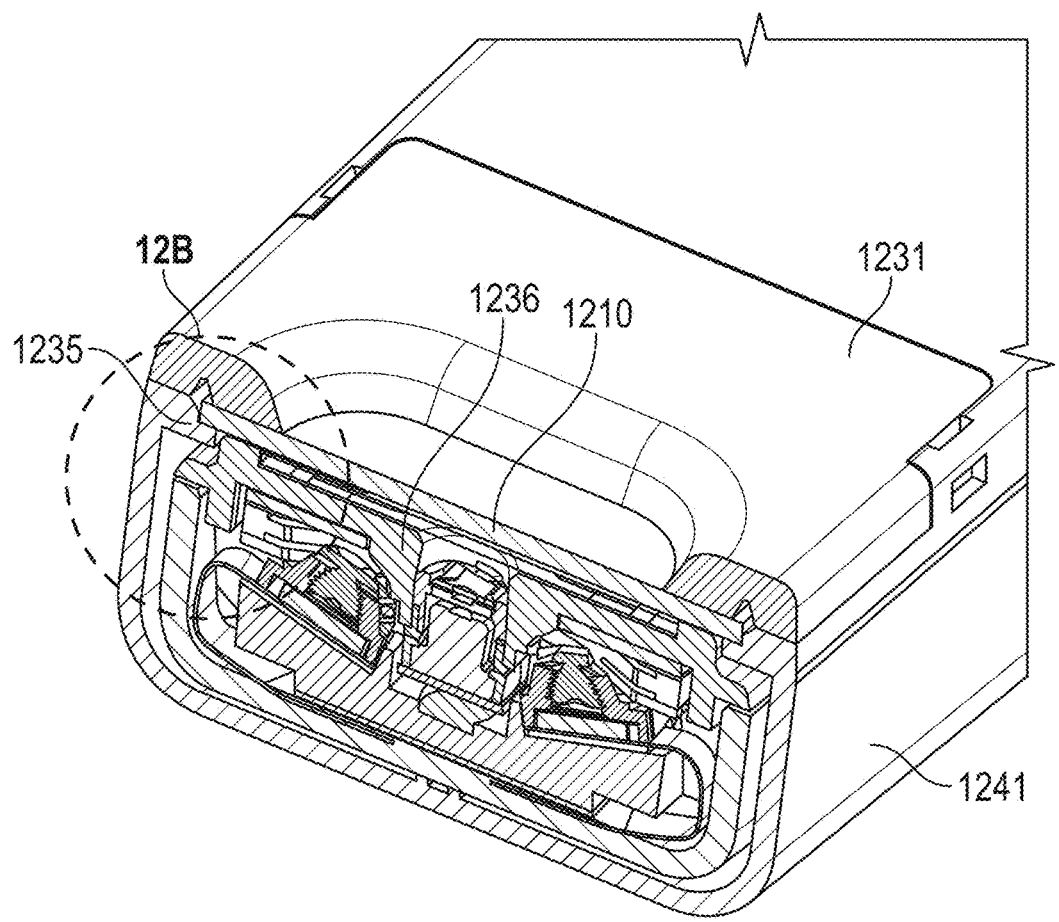
FIG. 12A shows a section through one example of a sleeve including a sealing frame.
Figure 12B:
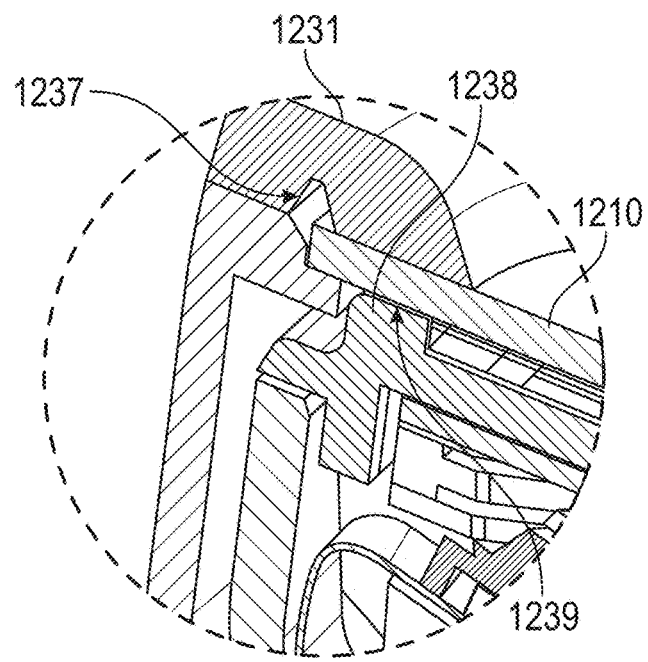
FIG. 12B is an enlarged view of region 12B of FIG. 12.

As mentioned, any of the sleeves described herein may include a sealing frame that may fit over a transparent cover (e.g., window) receiving area around the window region. FIGS. 12A-12B illustrate a section through another example of a sleeve in which a wan of an intraoral scanner 1236 has been inserted. In FIG. 12A the sleeve includes a receiving area 1235 and a sealing frame 1231 that is shown coupled to an outside of the elongate and hollow body 1241 of the sleeve so that the transparent cover 1210 is sandwiched between a periphery (e.g., the receiving or seating area 1235, which may be a lip or ledge) of the window opening and a sealing frame window opening. FIG. 12B shows an enlarged view of region 12B of FIG. 12A.

As shown in FIG. 12B, the sealing frame 1231 may include a channel or passage 1237 ("adhesive ditch") within which an adhesive material (e.g., gel, liquid, etc.) may be applied to secure the transparent cover over the window opening, e.g., by sealing between the sealing frame and the receiving area 1235 around the window. Thus, either or both the sealing frame and the body of the sleeve (e.g., the receiving area or the region adjacent to the receiving area) may include an adhesive channel that may peripherally surround at least partially around the sealing frame window opening, allowing holding an adhesive securing the transparent cover within the window opening.

In some examples, when the wand is fully engaged with the sleeve, the wand may include portion on or adjacent to the imaging window of the wand through which images may be captured that may rest against the transparent cover. For example, in FIG. 12B, the wand may include a metal spacing projection 1238 adjacent to the imaging window of the wand that may sit directly against 1239 the transparent cover of the sleeve, as shown. In some variations this connection may allow for anti-fogging (e.g., heating) of the transparent cover. This configuration, in which a portion of the wand contacts (e.g., presses against) the wand may be configured so that the imaging window of the wand is precisely positioned relative to the window of the sleeve. The spacing projection 1238 of the wand contacting the window may be referred to as a spacing portion or spacing projection of the wand, and may be metal or non-metal (e.g., plastic).

Figure 13A:
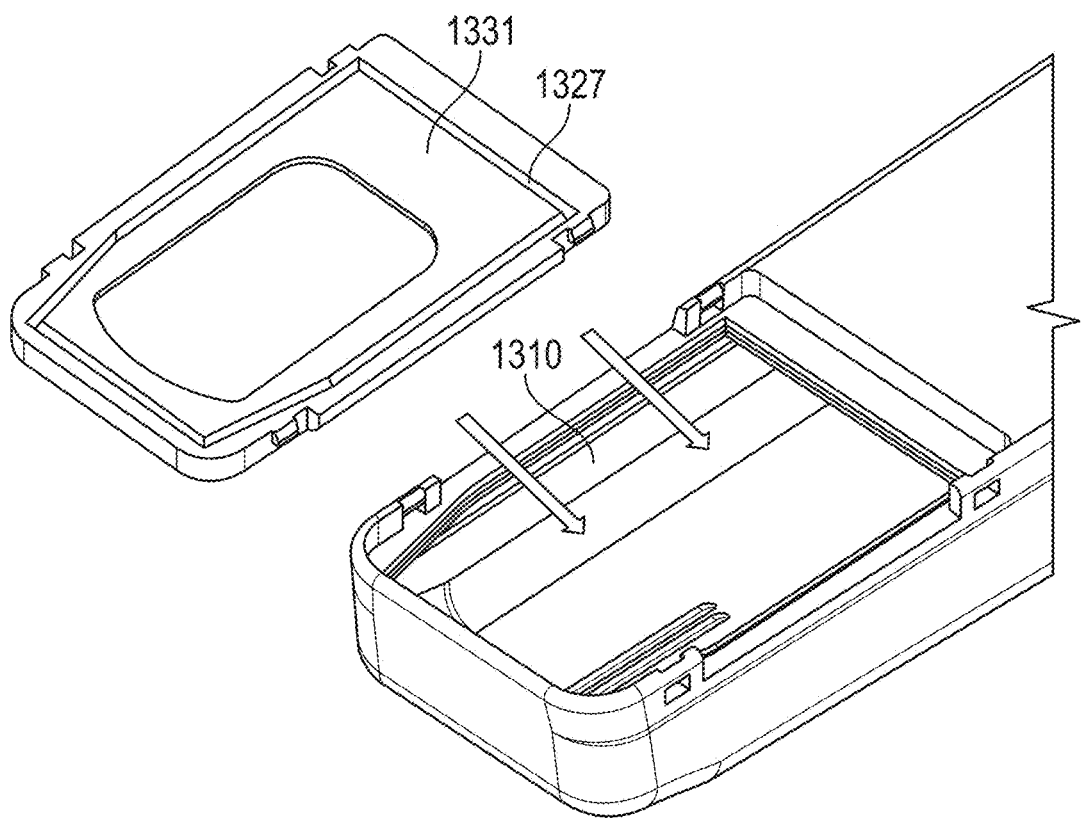
FIG. 13A illustrates the attachment of a sealing frame over a transparent cover of a sleeve in one example of a sleeve.
Figure 13B:
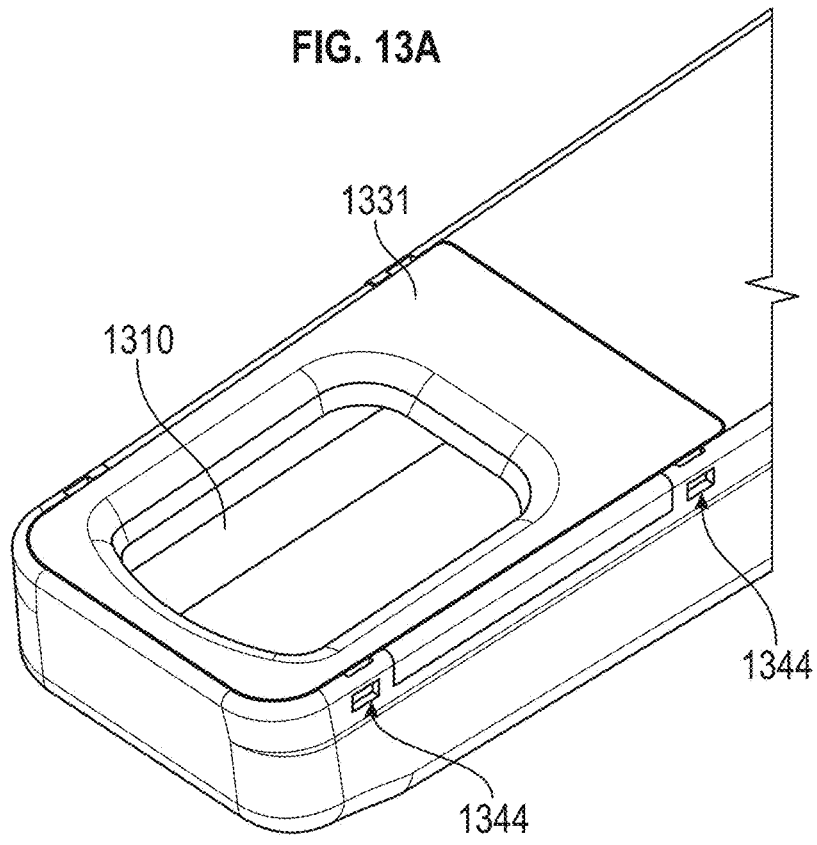
FIG. 13B shows the assembled sleeve of FIG. 13A with the sealing frame secured over the transparent cover.

The sealing frame 1231 may be secured to the body of the sleeve (the rigid or semi-rigid distal portion of the sleeve) by an adhesive and/or by a mechanical fastener such as a snap or the like. For example, FIGS. 13A-13B illustrate another example of a sleeve including a sealing frame 1331 that seals a transparent cover 1310. The window may be placed into the seating region of the sleeve, which is sized and configured to receive the transparent cover as shown. The transparent cover may be easily positioned without requiring force (pressure) to be applied. Once seated in the receiving area (e.g., the seating area or region, such as a lip or rim), an adhesive may be applied to the periphery of the sealing frame 1311 such as within a channel ("adhesive ditch") 1327 and the sealing frame 1331 may be applied over and into the receiving area of the sleeve as shown in FIG. 13B. In FIGS. 13A-13B the receiving area 1331 is recessed so that the sealing frame sits flush with the outer surface of the sleeve when the sealing frame is secured down. The sealing frame may also or alternatively be secured to the rest of the sleeve by one or more snaps 1344. In examples in which a frame is used, the frame may mechanically hold the transparent cover in place until the adhesive is cured, without requiring a fixing jig.

Figure 14:
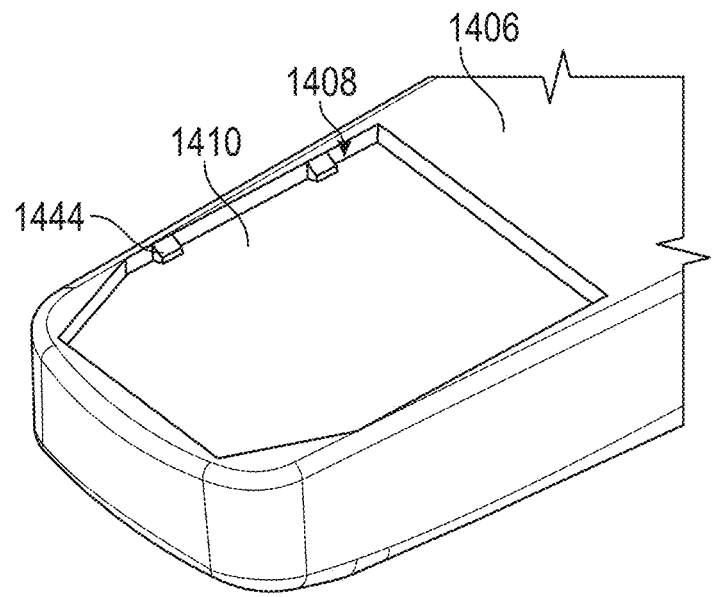
FIG. 14 is an example of a sleeve including snaps within the perimeter of the window region for securing a transparent cover.
Figure 15:
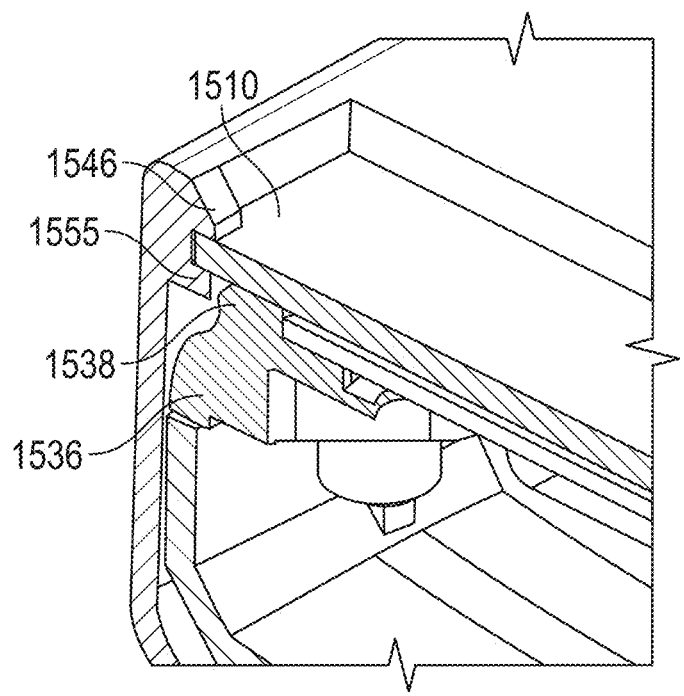
FIG. 15 shows a section through a sleeve similar to that shown in FIG. 14 in which a wand of an intraoral scanner has been inserted into the sleeve.

In some examples the sleeve may include a receiving area in the distal region of the body of the sleeve around the window opening of the sleeve that is configured to receive and hold a transparent cover without requiring a sealing frame. In some examples the transparent window is secured by an adhesive applied around the window opening 1408 of the body of the sleeve 1406 either before or after the transparent window has been applied. For example, FIG. 14 shows one variations of a sleeve in which a seating region is included at the distal end. The window region includes a peripheral seating area in which one or more snaps are included. The snaps are formed from the sleeve body (as a unitary portion) and may include a ramped overhang portion 1546 and an undercut region; the transparent cover 1510 edge may slide against the ramped overhang portion and displace (e.g., bend) it out of the way (or may itself bend out of the way) so that it may seat into the seating region 1535, as shown in FIG. 15. An adhesive may be applied around the periphery of the window opening to seal the transparent cover within the window opening (not shown). FIG. 15 also shows a section through the sleeve while the sleeve is being worn over a wand of an intraoral scanner 1536. In this example the wand also includes one or more spacing projection regions 1538 that may contact the transparent cover 1510.

Figure 16:
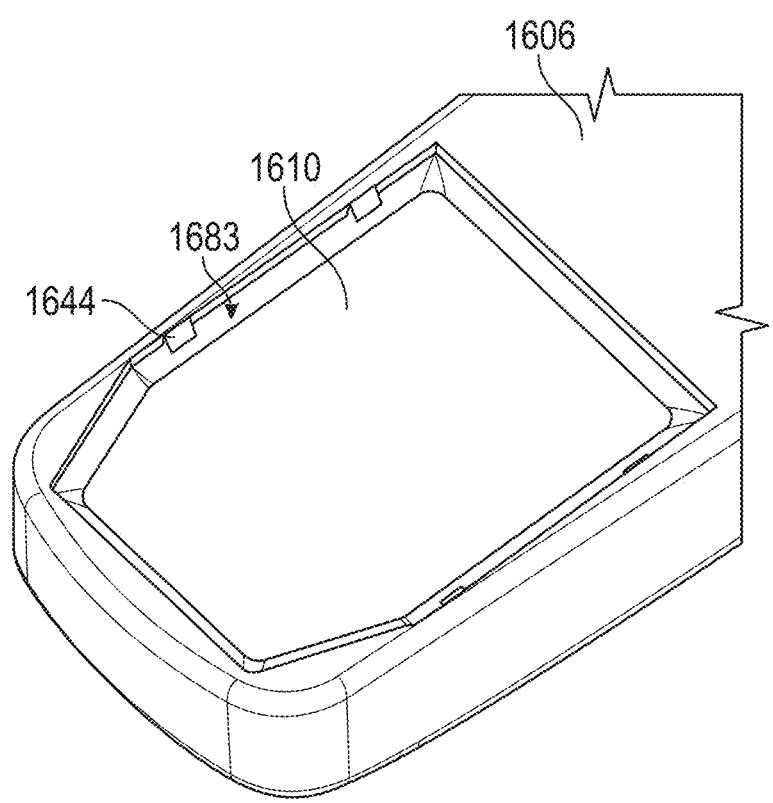
FIG. 16 shows a distal of another example of a sleeve similar to the one shown in FIG. 14 with the transparent cover inserted and a seal applied (e.g., an adhesive seal) around the perimeter of the window opening.

The adhesive may be added at the end, and from the outside, which may reduce the risk of contamination of any of the optics (e.g., windows) and may be easier and less expensive. For example, FIG. 16 illustrates the sleeve of FIG. 15 with an adhesive seal 1683 (which may be fully cured) shown. In FIG. 16 the transparent cover (window 1610) is held in place by the snaps 1644 formed integrally into the body along with the seating region of the sleeve 1606. In some examples one of the sides of the window opening may include a shelf and an overhang rather than a snap; the overhang may secure the transparent cover on one side and one or more snaps may be on the opposite side of the window opening and shelf (seating area).

Figure 17A:
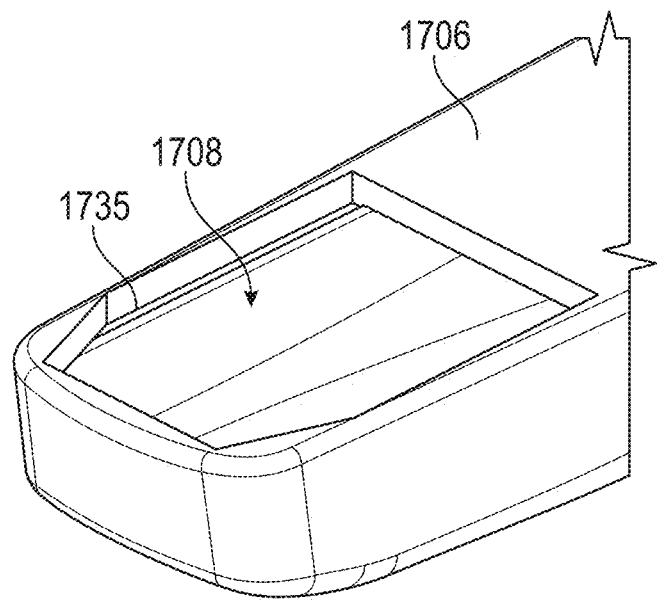
FIGS. 17A-17D illustrate the assembly of another example of a sleeve, in which the transparent cover is applied from the outside of the sleeve and secured in place using a heat press.
Figure 17B:
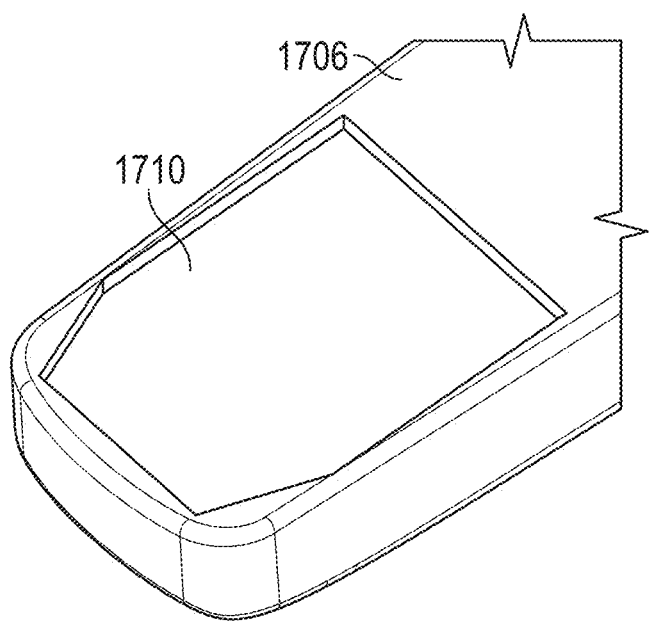
Figure 17C:
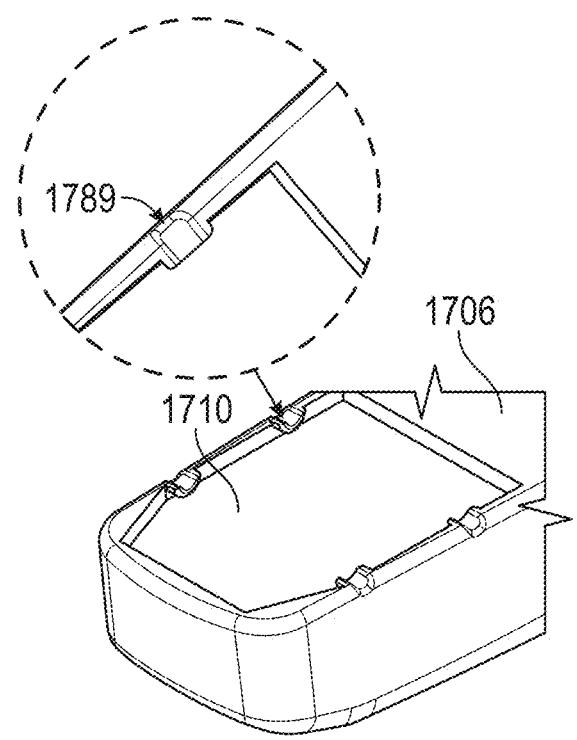
Figure 17D:
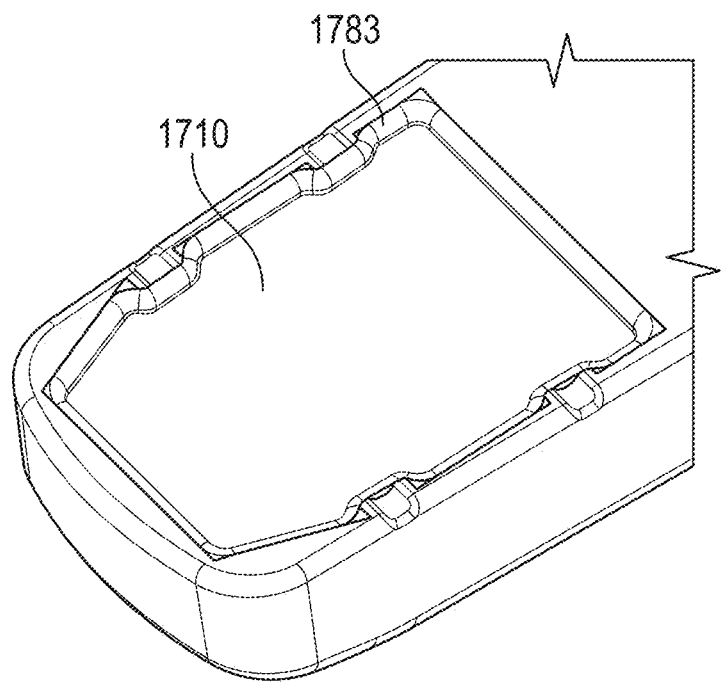

Also described herein are examples in which rather than (or in addition to) snaps, the transparent cover may be secured to the sleeve within a seating area 1735 by heat pressing to deform a region of the window perimeter of the sleeve, holding the transparent cover in place. FIGS. 17A-17D illustrate one example of a sleeve in which the transparent cover is heat-pressed (heat staked) in position. In FIG. 17A, the body of the sleeve 1706 includes a window opening 1708 with a seating area 1735 having a lip around the perimeter of the window opening. A transparent cover that fits the seating area (in size and shape) may be positioned onto the seating area from outside of the sleeve, as shown in FIG. 17B. FIG. 17C shows that multiple regions of the periphery may then be deformed to secure the transparent cover within the seating area, by (in one example) heat pressing. A heat may be applied at one or more points to melt and deform the polymeric peripheral region so that it forms a heat stake 1789 that extends over and locks the transparent cover in position, as shown. An adhesive sealing material 1783 may then be applied to seal the edges of the transparent window 1710 to the sleeve, as shown in FIG. 17D. Similar to the snap-fit configuration shown in FIGS. 14-16, this sleeve example may also be formed as a single injected part implementation into which the transparent window may be attached.

Figure 18A:
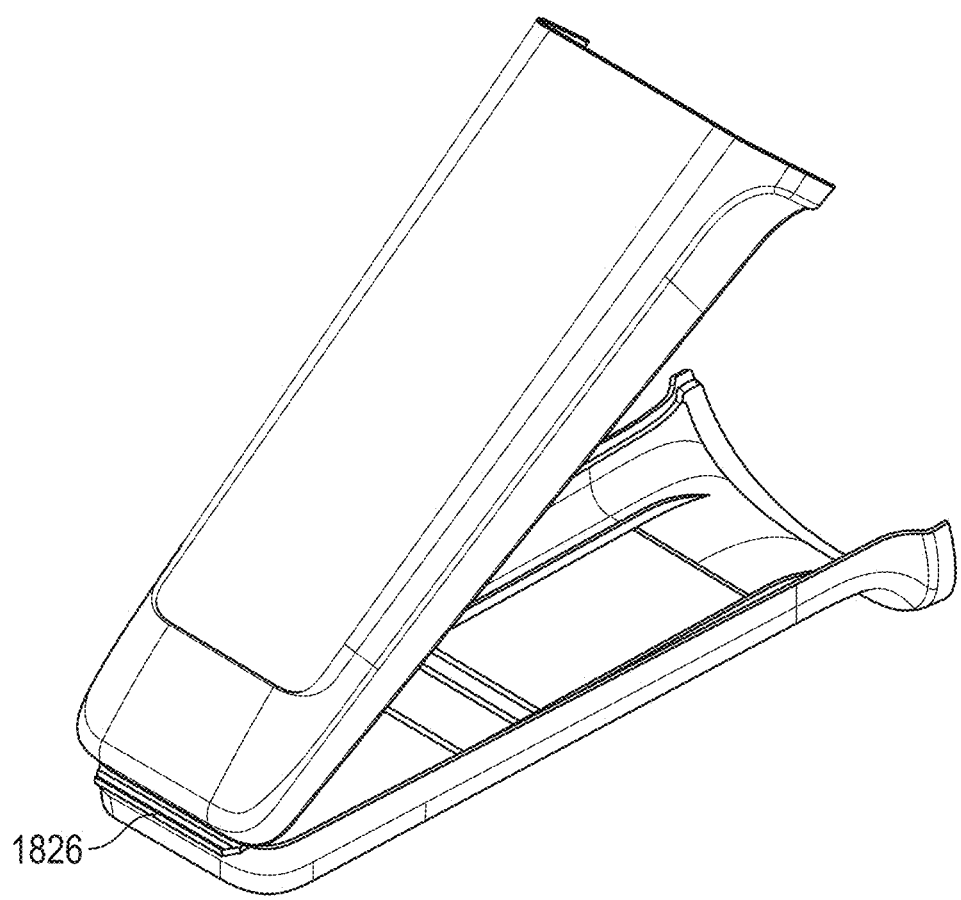
FIGS. 18A and 18B show an example of a sleeve configured as a clamshell having a living hinge.
Figure 18B:
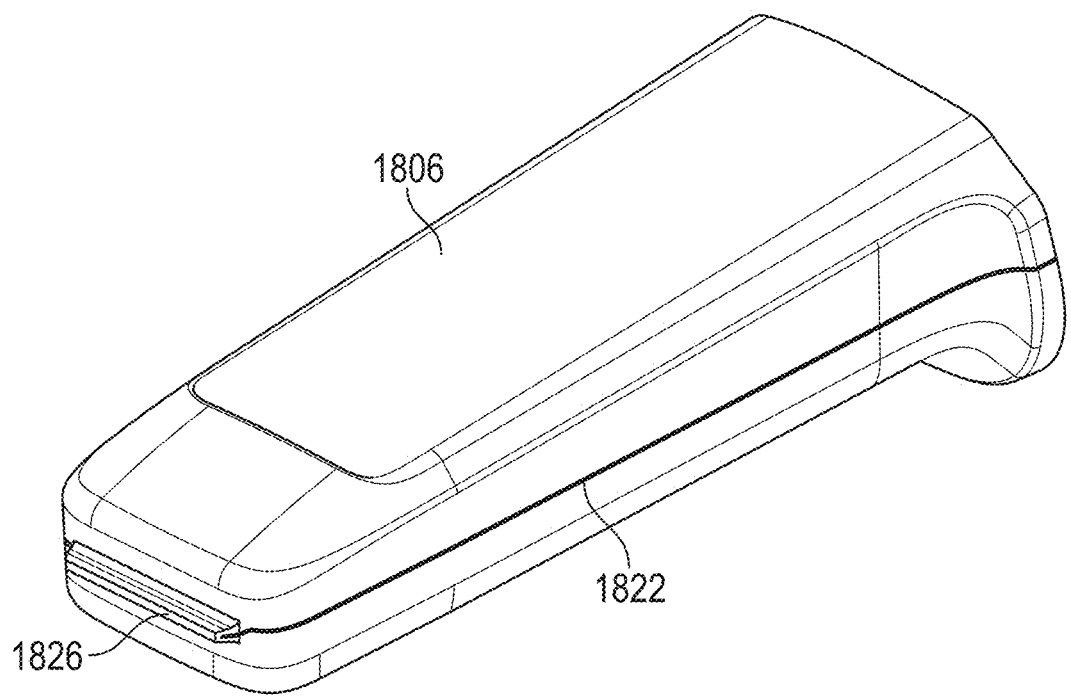
Figure 19A:
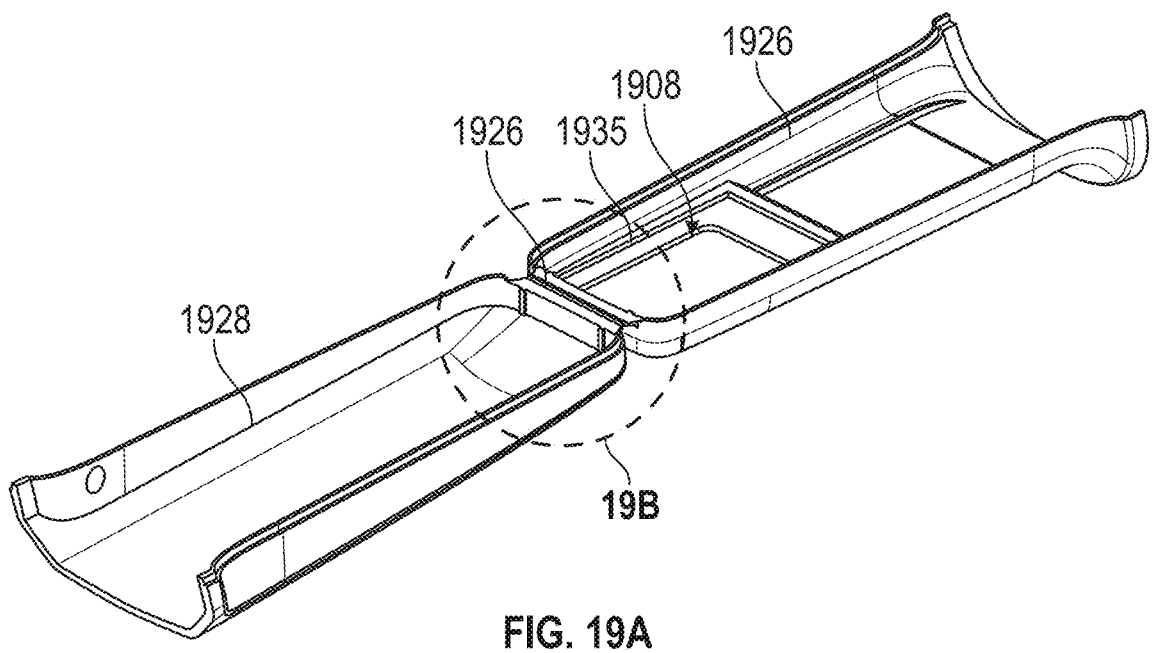
FIG. 19A shows another example of a sleeve including a living hinge, similar to that shown in FIG. 18A-18B.
Figure 19B:
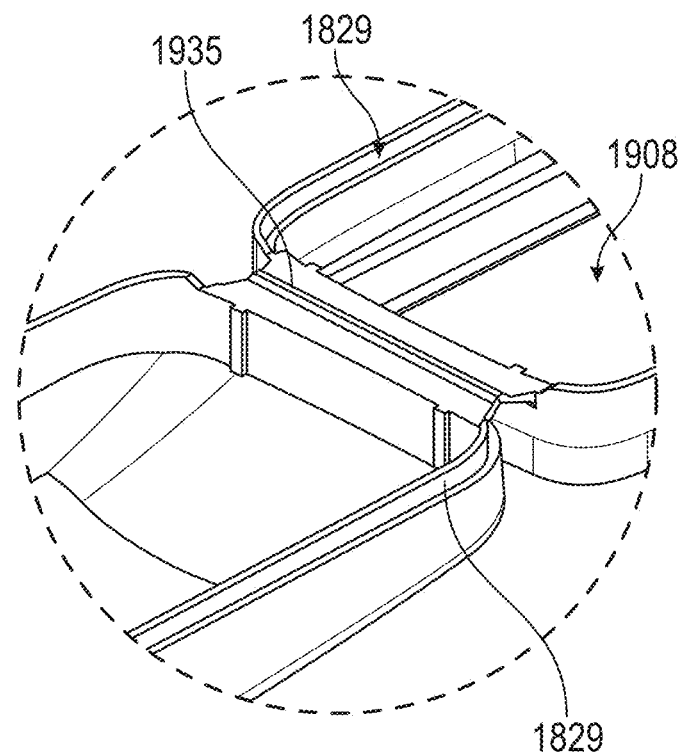
FIG. 19B is an enlarged view of region 19B of FIG. 19A, showing the living hinge in greater detail.

In some examples the transparent cover forming the window may be applied internally without having to be applied through the inside of the sleeve. For example, FIGS. 18A and 18B illustrate an example of a sleeve having a body that is formed as a clamshell including a living hinge region that may be molded or otherwise formed as a single piece (e.g., by injection molding) and may be closed along the living hinge to form the hollow sleeve (e.g., the distal, rigid/semi-rigid sleeve portion). FIG. 18A shows the body prior to closing (or during closing) while FIG. 18B shows the sleeve in the closed configuration. The edges 1822 of the sleeve 1806 where the two halves of the sleeve come together may be sealed, using an adhesive or by welding (e.g., laser welding) of the material. In this example the living hinge 1826 is on a distal end; in some examples the living hinge may be on a side and the top region may be sealed. FIGS. 19A and 19B illustrate an example of a sleeve body similar to that shown in FIGS. 18A-18B prior to folding about the hinge region 1926. In FIG. 19A the body includes two halves forming the front 1926 and back 1928 of the sleeve, separated by a living hinge. The window opening 1908 through the front side is included. In this example the window opening includes a seating area 1935 on the inner side of the sleeve in which the transparent cover may be positioned and secured. Region 19B is shown in greater detail in FIG. 19B. In some examples the edge of the front and back sides of the sleeve may be configured to mate with each other with a friction fit (e.g., by including lips or ridges 1829 that may engage with each other when assembled and closed together). This region may be welded as mentioned above.

Figure 20B:
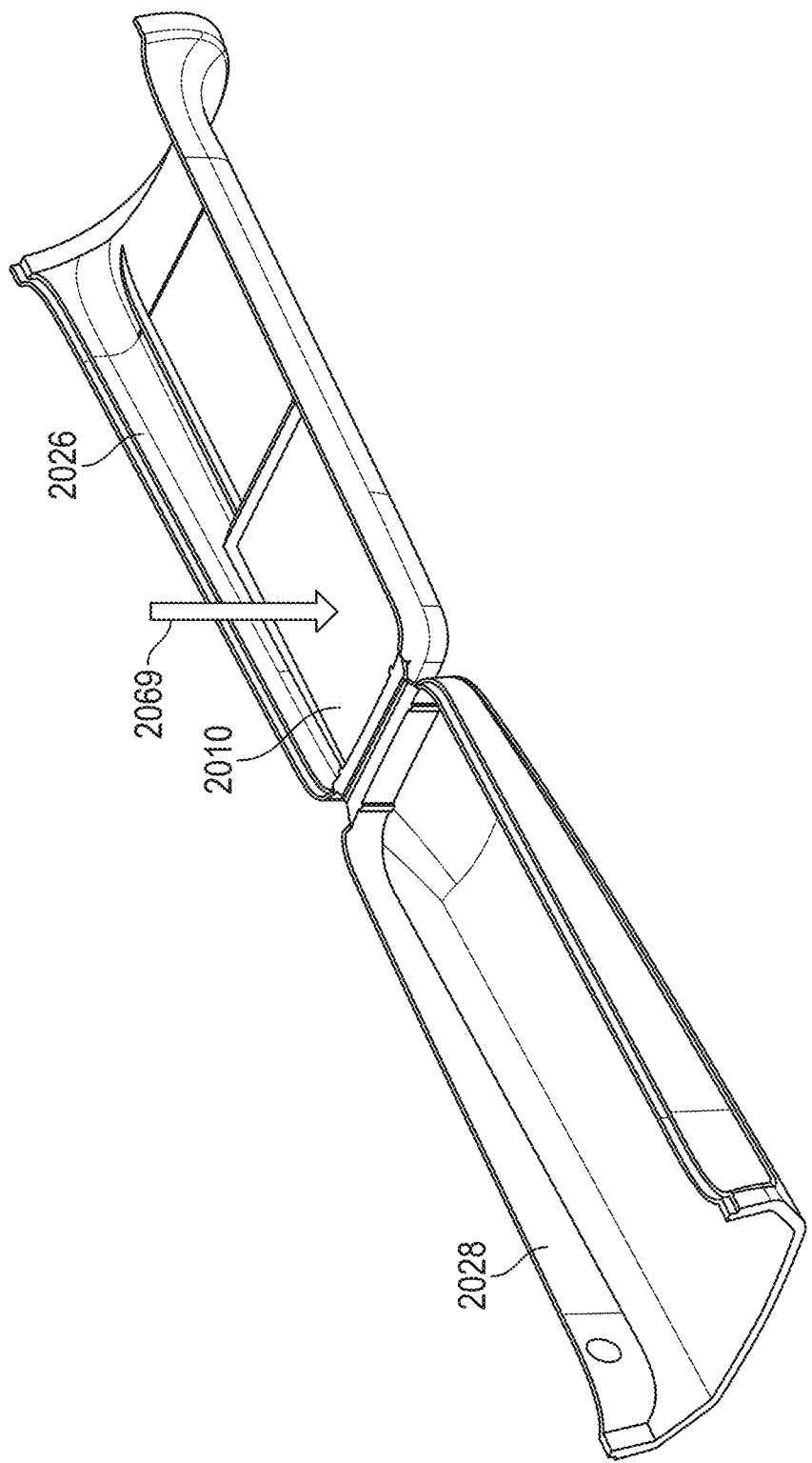
Figure 20C:
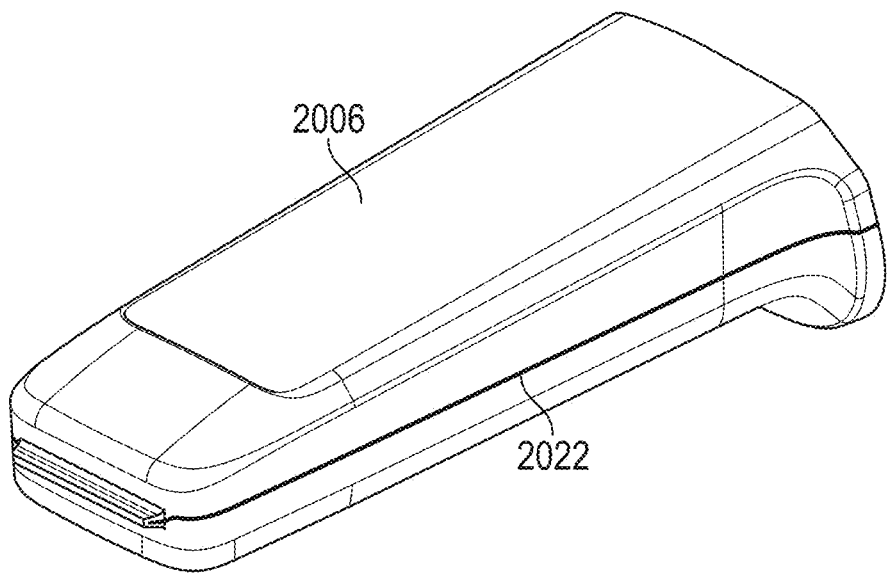

Prior to closing and sealing, the transparent cover may be added, as illustrated in FIGS. 20A and 20B. In this example an adhesive may be applied in the seating area 2035 and the transparent cover 2010 may be placed 2069 onto the seating area, as shown in FIG. 20B. The body may then be folded (by folding the top 2026 together with the bottom 2028) to form the closed and sleeve 2006, as shown in FIG. 20C, and the closed edges 2022 may be sealed, as mentioned above.

Figure 21A:
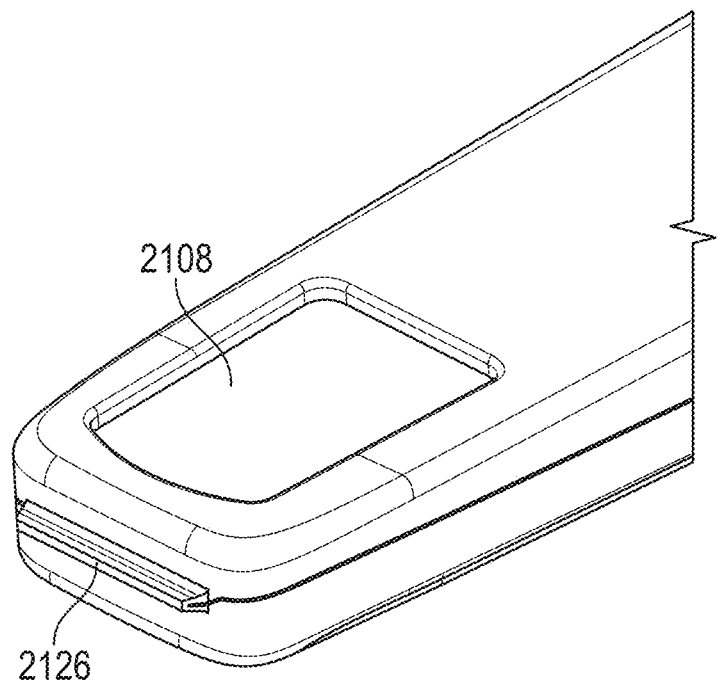
FIGS. 21A and 21B show front perspective and back perspective views, respectively of the distal end of another example of a sleeve for an intraoral scanner including a living hinge at the distal end region.
Figure 21B:
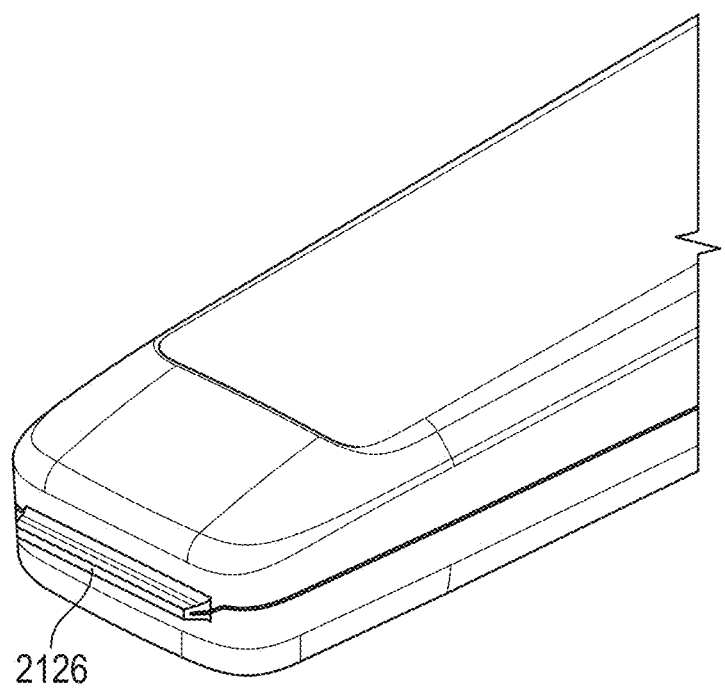

In any of the examples described herein, a sleeve extension may optionally be added. FIGS. 21A and 21B show the distal end, including the hinge region (configured as a living hinge in this example) in greater detail. FIG. 21A shows the front, including the window formed by the transparent cover 2110. FIG. 21B shows the back.

In general, any of the sleeves described herein may include features shown in any of these examples. Other sleeve designs may also incorporate all or some of these features. For example, in some cases the sleeve may be fabricated as a single piece, including the transparent window; for example, the entire sleeve (e.g., the sleeve distal end in regions including a sleeve extension) may be transparent. For example a transparent sleeve including an integral transparent cover may include the internal guiding structure (e.g., ramp) as described herein.

The sleeves described herein may be configured to withstand pressure of at least about 50 kPa, such as at least about 60 kPa, at least about 70 kPa, at least about 80 kPa, at least about 90 kPa, at least about 100 kPa, etc. In any of these sleeves the sleeve may be configured, e.g., by the position of the seating area for the window, so that there is a minimum separation between the sleeve window (transparent cover) and the imaging window of the wand. For example, the minimum clearance between the sleeve window and the imaging window may be about 0.1 mm, about 0.2 mm, about 0.3 mm, etc. This minimum distance may also be maintained in part based on a spacing projection adjacent to the imaging window of the wand, as described above.

Any of the sleeves described herein may include a flavor. For example, the sleeve (particularly the distal end region) may be coated or may incorporate a flavorant. Any appropriate flavorant may be used. Flavorants may be coated by dipping, spraying or the like.

As described above, in any of the variations described herein the systems and/or sleeves described herein may be configured for single, one-time (e.g., one continuous session) or a limited duration of time use.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A sleeve for an intraoral scanner, the sleeve comprising:
an elongate and hollow body having a distal end and a proximal end, wherein the distal end is tapered and closed and the proximal end is open to receive an intraoral scanner;
a window opening on a lateral side of the distal end;
a transparent cover over the window opening; and
a ramp formed integrally within the elongate and hollow body, the ramp including a plurality of ribs extending in a proximal to distal direction and having a distal facing ramp angle and a proximal facing ramp angle greater than the distal facing ramp angle, and wherein the ramp is positioned within the hollow body proximal to the window opening, and configured to guide a distal end of the intraoral scanner away from the window opening as the intraoral scanner is inserted into the sleeve.

2. The sleeve of claim 1, further comprising a foam at least partially circumferentially around the window opening within the hollow body, wherein the transparent cover is secured against the foam.

3. The sleeve of claim 1, further comprising one or more projections configured to impinge into a field of view of the intraoral scanner from a periphery of the window into the window opening when the intraoral scanner is engaged with the sleeve.

4. The sleeve of claim 1, further comprising a sleeve extension extending from the proximal end of the elongate and hollow body.

5. The sleeve of claim 4, wherein the sleeve extension is configured to invert over itself when pulled distally.

6. The sleeve of claim 1 wherein the sleeve is formed of a polyethylene material.

7. The sleeve of claim 1, further comprising an adhesive seal around the window opening sealing the transparent cover to the window opening.

8. The sleeve of claim 1, further comprising a sealing frame coupled to an outside of the elongate and hollow body so that the transparent cover is sandwiched between a periphery of the window opening and a sealing frame window opening.

9. The sleeve of claim 8, wherein the sealing frame is coupled to the elongate and hollow body by one or more snap fits.

10. The sleeve of claim 8, wherein the sealing frame comprises an adhesive channel peripherally arranged around the sealing frame window opening.

11. The sleeve of claim 8, wherein the elongate and hollow body comprises a seating region configured to hold the transparent cover, further wherein the sealing frame is configured to secure to the seating region so that an outer surface of the sealing frame is flush with an outer surface of the elongate and hollow body.

12. The sleeve of claim 1, wherein the elongate and hollow body comprises a seating region configured to hold the transparent cover, further comprising a plurality of snaps projecting into the seating region from a periphery of the window opening, wherein the plurality of snaps are configured to secure the transparent cover within the seating region.

13. The sleeve of claim 1, wherein the elongate and hollow body comprises a seating region configured to hold the transparent cover, further wherein the window opening comprises a plurality of heat-press detents projecting into the window opening from a periphery of the window opening, wherein the heat-press detents are configured to secure the transparent cover within the seating region.

14. The sleeve of claim 1, wherein the elongate and hollow body comprises a clamshell body having a living hinge at the distal end of the elongate and hollow body, further wherein a lateral seam on either side of the elongate and hollow body is sealed closed.

15. The sleeve of claim 1, wherein the sleeve comprises a flavorant to give the sleeve a flavor.

16. The sleeve of claim 1, wherein the ramp is offset from the window opening by a predetermined distance.

17. The sleeve of claim 1, wherein the distal facing ramp angle is between ten and fifty degrees.

18. A sleeve for an intraoral scanner, the sleeve comprising:
an elongate and hollow body having a distal end and a proximal end, wherein the distal end is tapered and closed and the proximal end is open to receive an intraoral scanner;
a window opening on a lateral side of the distal end;
a transparent cover over the window opening;
a sealing frame coupled to an outside of the elongate and hollow body so that the transparent cover is sandwiched between a periphery of the window opening and a sealing frame window opening;
an adhesive channel peripherally at least partially around the sealing frame window opening holding an adhesive securing the transparent cover within the window opening; and
a ramp formed integrally within the elongate and hollow body, the ramp including a plurality of ribs extending in a proximal to distal direction and having a distal facing ramp angle and a proximal facing ramp angle greater than the distal facing ramp angle, wherein the ramp is configured to guide a distal end of the intraoral scanner away from the window opening as the intraoral scanner is inserted into the sleeve.

19. The sleeve of claim 18, wherein the sealing frame is coupled to the elongate and hollow body by one or more snap fits.

20. The sleeve of claim 18, wherein the elongate and hollow body comprises a seating region configured to hold the transparent cover, further wherein the sealing frame is configured to secure to the seating region so that an outer surface of the sealing frame is flush with an outer surface of the elongate and hollow body.

21. The sleeve of claim 18, further comprising one or more projections configured to impinge into a field of view of the intraoral scanner from a periphery of the window into the window opening when the intraoral scanner is engaged with the sleeve.

22. The sleeve of claim 18, further comprising a sleeve extension extending from the proximal end of the elongate and hollow body.

23. The sleeve of claim 22, wherein the sleeve extension is configured to invert over itself when pulled distally.

24. The sleeve of claim 18 wherein the sleeve is formed of a polyethylene material.

25. A sleeve for an intraoral scanner, the sleeve comprising:
an elongate and hollow body having a distal end and a proximal end, wherein the distal end is tapered and closed and the proximal end is open to receive an intraoral scanner;
a window opening on a lateral side of the distal end;
a transparent cover over the window opening; and a ramp formed integrally within the elongate and hollow body, the ramp including a plurality of ribs extending in a proximal to distal direction and having a distal facing ramp angle and a proximal facing ramp angle greater than the distal facing ramp angle, wherein the ramp is configured to guide a distal end of the intraoral scanner away from the window opening as the intraoral scanner is inserted into the sleeve, and wherein the elongate and hollow body comprises a clamshell body having a living hinge at the distal end of the elongate and hollow body, further wherein a lateral seam on either side of the elongate and hollow body is sealed closed.

26. The sleeve of claim 25, further comprising a foam at least partially circumferentially around the window opening within the hollow body, wherein the transparent cover is secured against the foam.

27. The sleeve of claim 25, further comprising one or more projections configured to impinge into a field of view of the intraoral scanner from a periphery of the window into the window opening when the intraoral scanner is engaged with the sleeve.

28. The sleeve of claim 25, further comprising a sleeve extension extending from the proximal end of the elongate and hollow body.

29. The sleeve of claim 28, wherein the sleeve extension is configured to invert over itself when pulled distally.

30. The sleeve of claim 25 wherein the sleeve is formed of a polyethylene material.

31. The sleeve of claim 25, further comprising an adhesive seal around the window opening sealing the transparent cover to the window opening.

32. The sleeve of claim 25, wherein the elongate and hollow body comprises a seating region configured to hold the transparent cover, further comprising a plurality of snaps projecting into the seating region from a periphery of the window opening, wherein the plurality of snaps are configured to secure the transparent cover within the seating region.

33. The sleeve of claim 25, wherein the elongate and hollow body comprises a seating region configured to hold the transparent cover, further wherein the window opening comprises a plurality of heat-press detents projecting into the window opening from a periphery of the window opening, wherein the heat-press detents are configured to secure the transparent cover within the seating region.

34. The sleeve of claim 25, wherein the sleeve comprises a flavorant to give the sleeve a flavor.

* * * * *